(12) United States Patent
Guarna et al.

(10) Patent No.: US 8,809,338 B2
(45) Date of Patent: Aug. 19, 2014

(54) 1,2,3-TRIAZOLE-BASED PEPTIDOMIMETIC INTEGRIN INHIBITORS FOR THE DIAGNOSIS AND THERAPY OF TUMORS

(75) Inventors: Antonio Guarna, Servezza (IT); Gloria Menchi, Sesto Fiorentino (IT); Nicoletta Cini, Florence (IT); Andrea Trabocchi, Florence (IT); Alberto Pupi, Florence (IT); Anna Bottoncetti, Bagno a Ripoli (IT); Silvia Raspanti, Florence (IT); Lido Calorini, Florence (IT)

(73) Assignee: Universita' Degli Studi di Firenze, Florence (IT)

( * ) Notice: Subject to any disclaimer, the term of this patent is extended or adjusted under 35 U.S.C. 154(b) by 0 days.

(21) Appl. No.: 13/578,246

(22) PCT Filed: Feb. 14, 2011

(86) PCT No.: PCT/EP2011/052139
§ 371 (c)(1),
(2), (4) Date: Oct. 24, 2012

(87) PCT Pub. No.: WO2011/098603
PCT Pub. Date: Aug. 18, 2011

(65) Prior Publication Data
US 2013/0040964 A1    Feb. 14, 2013

(30) Foreign Application Priority Data
Feb. 12, 2010   (IT) ................................ FI2010A0019

(51) Int. Cl.
  *A61K 31/497*   (2006.01)
  *A61K 31/41*    (2006.01)
  *A61K 31/415*   (2006.01)

(52) U.S. Cl.
  USPC ....................... 514/254.05; 514/359; 514/394

(58) Field of Classification Search
  None
  See application file for complete search history.

(56) References Cited

FOREIGN PATENT DOCUMENTS

WO    WO2008/033557    3/2008

OTHER PUBLICATIONS

CAS RN 1243239-09-9 (entered into STN Sep. 28, 2010).*
Anderson (Chem and Biol 10:787-797, 2003).*
Thiel (Nature Biotechnol 2:513-519, 2004).*
Gong et al (Bioorg Med Chem 18:1331-1335, 2008).*
International Search Report for International App. No. PCT/EP2011/052139.
Cacciari et al., "Non Peptidic $\alpha_v\beta_3$ Antagonist: Recent Devleopments", Current Medicinal Chemistry 12, pp. 51-70, 2005.
Duggan et al., "Ligands to the integrin receptor $\alpha_v\beta_3$", Expert Opinion on Therapeutic Patents, Monthly Focus: Biololgicals, Immunologicals & Drug Delivery, pp. 1367-1383, Ashley Publications Ltd., 2000.
Coleman et al., "Ligands to the integrin receptor $\alpha_v\beta_3$," Expert Opinion, Monthly Focus: Pulmonary-Allergy, Dermatological, Gastrointestinal & Arthritis, pp. 1009-1021, Ashley Publications Ltd., 2002.
Absolute stereochemistry, XP-002632144, C:\EPOPROGS\ SEA\.\..\.. \epodata\sea\eplogf\SA1042130.1og, Aug. 4, 2011.
Trabocchi et al., "Click-Chemistry-Derived Triazole Ligands of Arginine-Glycine-Aspartate(RGD) Integrims with a Broad Capacity to Inhibit Adhesion of Melanoma Cells and both in Vitro and in Vivo Angiogenesis", Journal of Medicinal Chemistry, 53, pp. 7119-7128, 2010.

* cited by examiner

*Primary Examiner* — Craig Ricci
(74) *Attorney, Agent, or Firm* — DLA Piper LLP (US)

(57) ABSTRACT

The present invention refers to the field of chemical compounds bearing a 1,2,3-triazole ring of formula (I) and possessing guanidino and carboxylic groups or their isosteres, their preparation by Cu-catalyzed "click-chemistry", and medical-diagnostic use in pathologies where angiogenesis is altered, for example pathologic conditions of tumor origin, tumor metastasis, osteoporosis, and rheumatoid arthritis.

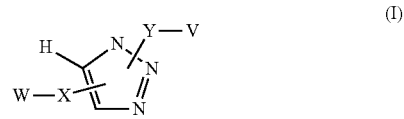

7 Claims, 3 Drawing Sheets

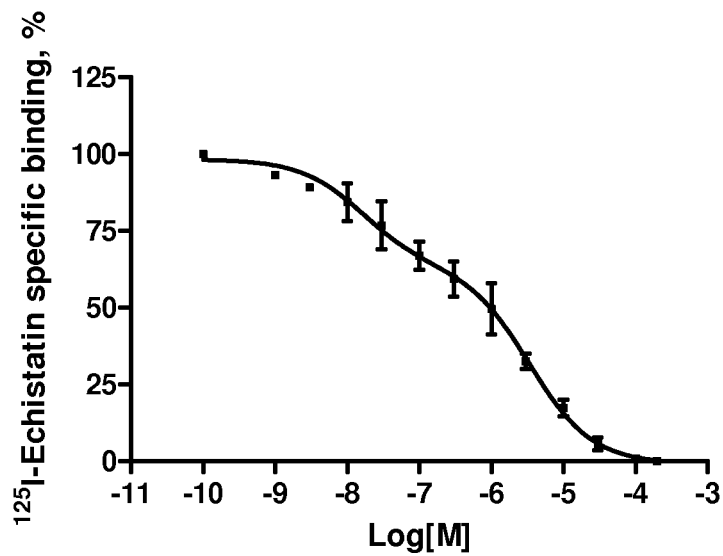
Figure 1a. Inhibition profile of compound 38 for αvβ3 integrin.
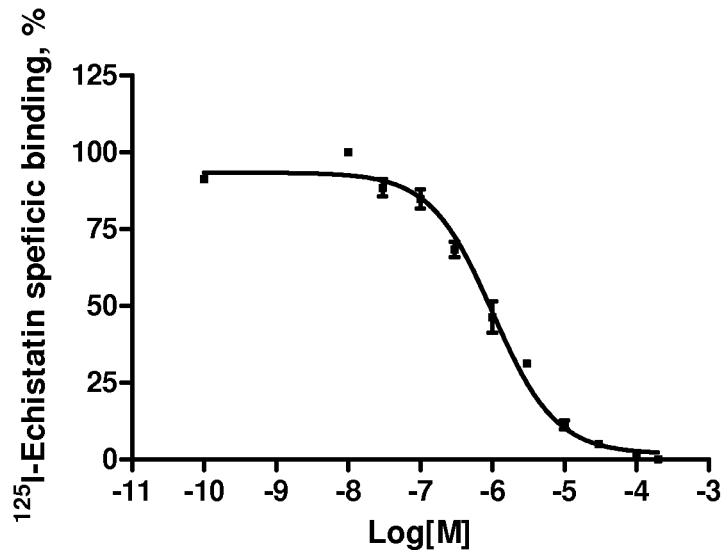
Figure 1b. Inhibition profile of compound 38 for αvβ5 integrin.

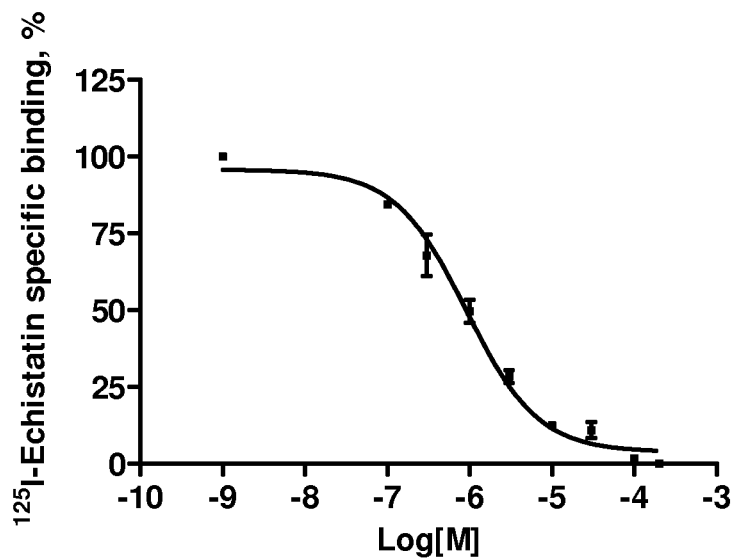
Figure 2a. Inhibition profile of compound 48 for αvβ3 integrin.
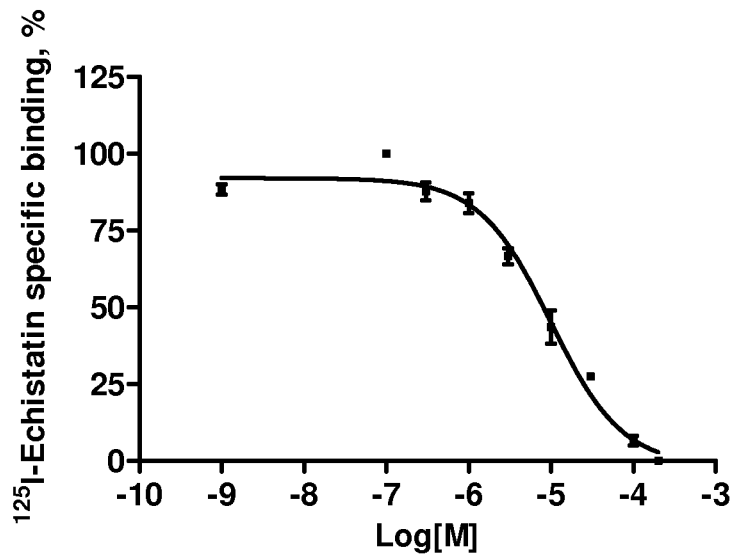
Figure 2b. Inhibition profile of compound 48 for αvβ5 integrin.

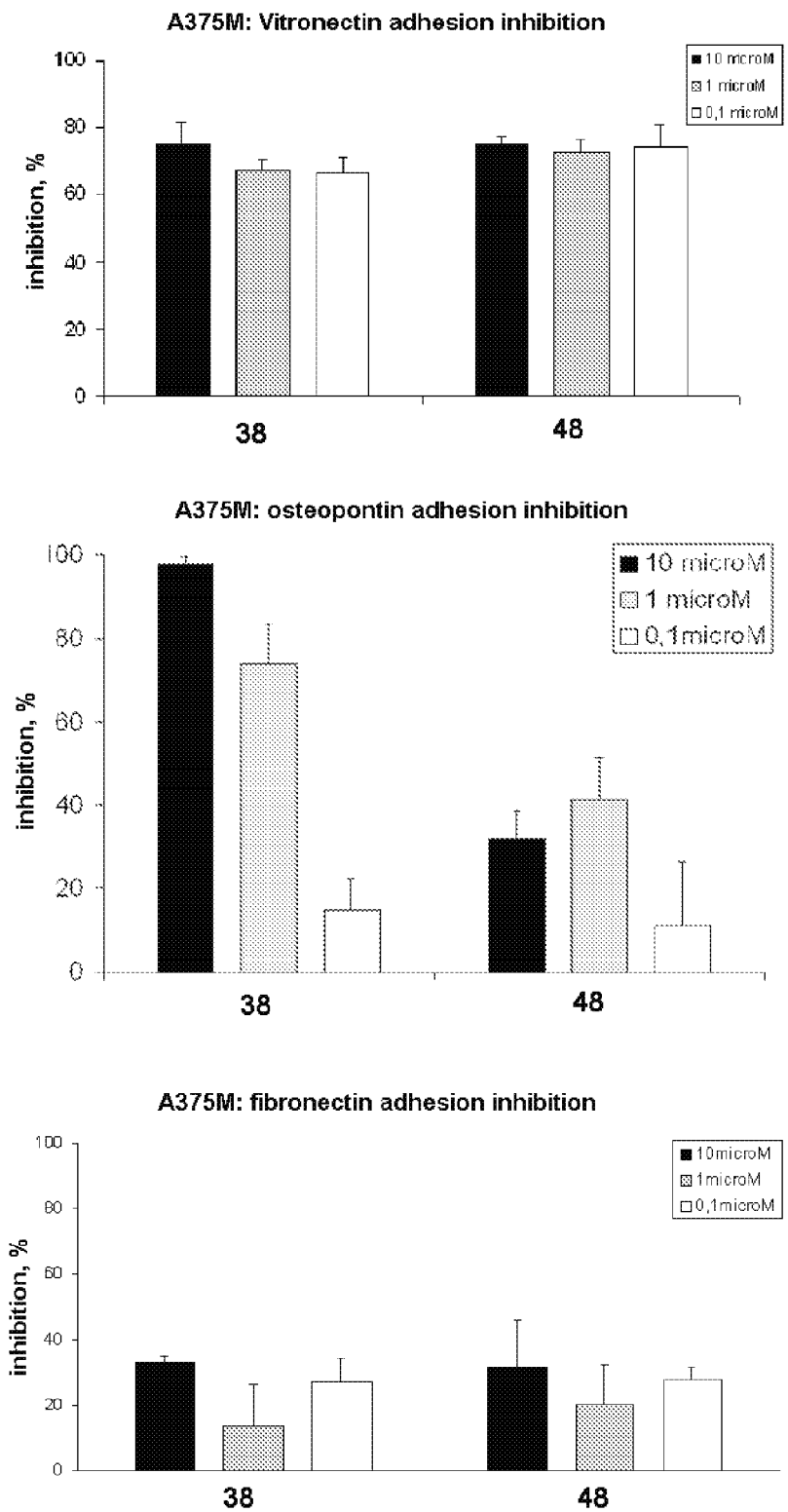
Figure 3. Cellular adhesion inhibition assays of compounds 38 and 48 for the A375M melanoma cell line.

1,2,3-TRIAZOLE-BASED PEPTIDOMIMETIC INTEGRIN INHIBITORS FOR THE DIAGNOSIS AND THERAPY OF TUMORS

FIELD OF INVENTION

The present invention refers to the field of chemical compounds possessing the 1,2,3-triazole heterocyclic ring, their preparation and use as a medical device for tumor-related pathologies where angiogenesis is altered, i.e. pathologies having a tumor origin, tumor methastasis, osteoporosis and rheumatoid arthritis.

STATE OF THE ART

Integrins are a class of cellular receptors known to bind extracellular matrix proteins, and therefore mediate cell adhesion events. One important recognition site of a ligand for αvβ3 and αvβ5 integrins is the arginine-glycine-aspartic acid (RGD) tripeptide sequence, which is found in all peptide-based ligands identified for the vitronectin receptor integrins. Among the RGD-dependent integrins, αvβ3 and αvβ5 receptors have received increasing attention as therapeutic targets as they are expressed in various cell types and are involved in osteoporosis, arthritis, retinopathy, and tumor-related processes. The RGD recognition site can be mimicked by polypeptides that contain the RGD sequence, and αvβ3 antagonists, including RGD-containing peptides, have been successfully applied as inhibitors of blood vessel development and tumor growth. During last years, the cyclic peptide c[RGDfV] has been reported by Kessler and co-workers as a selective ligand for the αvβ3 integrin. Many different cyclic RGD-containing peptides have been reported, and in particular, the N-methylated derivative c[RGDf(Me)Val] (Cilengitide), which is actually being examined in clinical trials as an angiogenesis inhibitor for the treatment of glioblastoma. Nevertheless, there is a need for alternative drugs capable of displaying a different activity profile in order to solve potential side effects outlined in present clinical trials (Reynolds, A. R. e collab. *Nat. Med.* 2009, 15, 392). Moreover, new molecular probes for the diagnosis of pathologies where integrins are involved are strongly requested.

During last years, several examples of peptidomimetic integrin inhibitors containing heterocyclic nuclei have been reported (Cacciari, B.; Spalluto, G. *Curr. Med. Chem.* 2005, 12, 51-70), including: benzodiazepinones, piperazines, benzoazepinones, nitroaryls, isoxazolines, indazoles, phenols, and others, with the exception of triazole derivatives.

The unique molecular system containing the triazole ring is a cyclic analogue of c[RGDfV] peptide, wherein the triazole ring is a replacement for the D-Phe-Val dipeptide, which solves only in part the issues concerning the chemical stability and bioavailability (Kolb, H.; Chen, K.; Walsh, J. C.; Gangadharmath, U.; Kasi, D.; Wang, B.; Duclos, B.; Liang, Q.; Padgett, H. C.; Karimi, F. WO2008/033557). No examples of linear non-peptidic integrin antagonists containing the 1,2,3-triazole ring have been reported, so far. There has been an increasing interest in the synthesis of molecules containing the triazole nucleus since the development by Sharpless and collab. of a catalytic method using Cu(I) as catalyst with or without sodium ascorbate for the generation of 1,4-disubstituted 1,2,3-triazole compounds from an alkyne and an azide under mild and high regioselective conditions (Sharpless, B. K.; Fokin, V.; Rostovsev, V.; Green, L.; Himo, F. WO03/101972). There is a need for new high affinity αvβ3 and αvβ5 integrin ligands in the diagnostic and medical field, which do not display a peptide character, are obtained by a straightforward synthetic method, and are capable of showing an antiangiogenic activity as a consequence of their antagonistic activity towards integrins. Thus, it is evident the need for a molecule metabolically more stable than present ligands based on the RGD peptide sequence, and of convenient and easy synthetic procedures starting from commercially available precursors in few synthetic steps.

Aim of the present invention is a compound possessing the above mentioned features, such as the simple preparation from easily-synthesized precursors, even as enantiopure compounds, being of wide scope so as to allow for the generation of derivatives with different properties, and possessing a significant metabolic stability, and a high affinity towards integrins related to an in vivo anti-angiogenic activity.

SUMMARY OF THE INVENTION

The present invention refers to peptidomimetic compounds containing the 1,2,3-triazole nucleus, and possessing high affinity towards αvβ3 and αvβ5 receptors of the integrins family.

The present invention refers to compounds of formula (I)

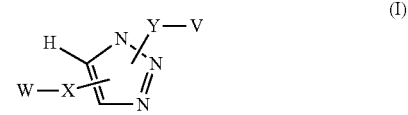

wherein

V is a COOH group or CONHOH;

W is a guanidino group or an isostere chosen in the group consisting of

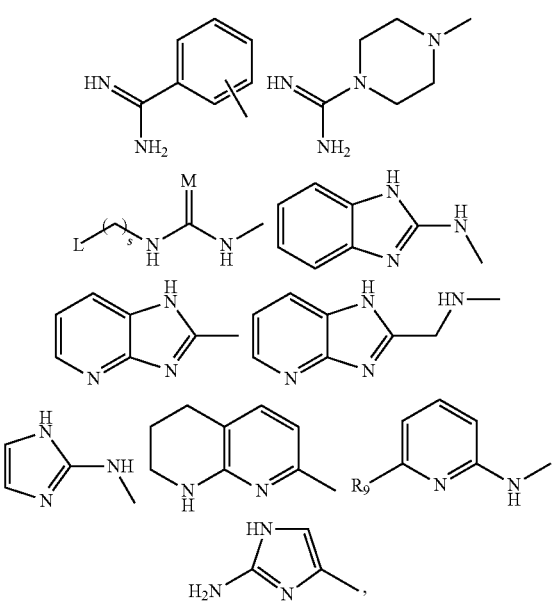

where M=O, NH; L=H, cycloalkyl, aryl optionally substituted, NH2, OH, SH, tyrosine, tyramine,

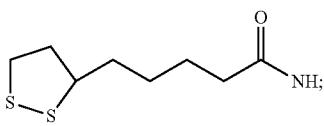

and s=0-8; R9=H, NH2, CH3, CF3; V—Y— is chosen in the group consisting of V—(CH2)p-CH(R5)-N(R4)-CO—(CH2)m-Q(R1)-(CH2)r-, V—(CH2)p-CH(R5)-N(R4)-(CH2)m-, V—(CH2)p-CH(R5)-N(R4)-CO—(CH2)m-,

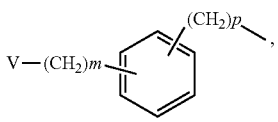

wherein Q=N, O; m e r are independently=1,2,3; p=0,1,2; if Q=N then R1=H, alkyl; if Q is O then R1 is absent; R4=H, alkyl, aryl optionally substituted, SO2aryl optionally substituted; R5=amino acid side chain, or is chosen in the group consisting of

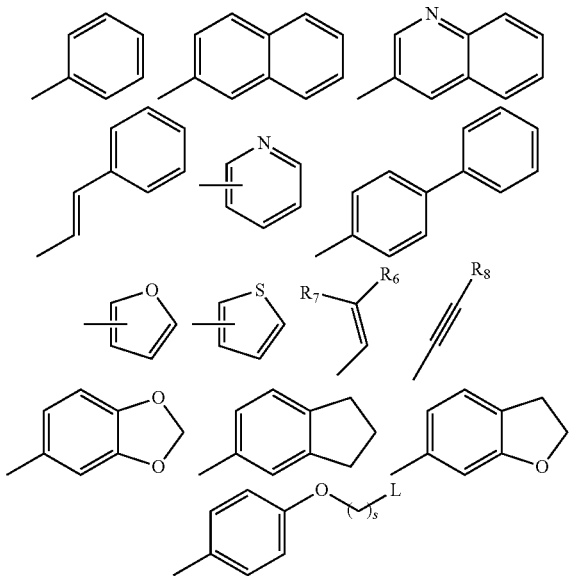

said rings being optionally substituted, where R6, R7 and R8 are independently chosen in the group consisting of H, alkyl, cycloalkyl; and L and s are defined as above;

W—X— is chosen in the group consisting of W—(CH2)n-, W—CO(CH2)n-,

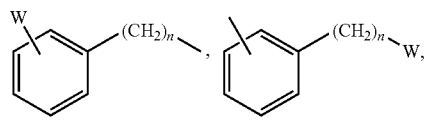

where n=1,2,3;

including all the possible variations of the stereogenic centers, pharmaceutically acceptable salts, and including the possible presence of one or more radioisotopes.

Surprisingly, they have been found to be potent integrin inhibitors, and in particular of integrins that recognize the Arg-Gly-Asp (RGD) peptide sequence, and more specifically of αvβ3 and αvβ5 integrins. Thus, they can be used in medicine, in particular for the preparation of diagnostic and/or therapeutics for the treatment of pathologies wherein the above-mentioned integrins are involved, particularly connected to angiogenesis, tumor initiation and growth, osteoporosis, and rheumatoid arthritis.

An aspect of the present invention deals with pharmaceutical preparations containing at least one compound of formula (I), and at least another pharmaceutically acceptable ingredient, eccipient, or diluent.

DEFINITIONS

According to the present invention within compounds of formula (I) as above defined:

The term "protecting group" means any functional group capable to preclude the atom to which it is bound to participate to an unwanted reaction or new bond formation, as usual in chemical synthesis. Preferred protecting group are those capable to inhibit the reactivity and new bond formation of oxygen, nitrogen, carboxylic acids, thiols, alcohols, amines and similar ones. Such groups, their preparation and use, are known to the state of the art, and they include, for example for the OH group: benzyl, t-butyl, acetals, esters, trialkylsilylethers; for the COOH group: methyl, t-butyl, benzyl, phenyl, allyl esters; for the NH group: t-Boc, Fmoc, Cbz, Alloc, Bn, Bz, Nosyl.

The term "amino acid side-chain" means the diverse substitution as a side chain linked to an "amino acid". The term "amino acid" includes all the 20 proteinogenic alpha-amino acids of the L or D series, and having as "side chain": —H for glycine; —CH3 for alanine; —CH(CH3)2 for valine; —CH2CH(CH3)2 for leucine; —CH(CH3)CH2CH3 for isoleucine; —CH2OH for serine; —CH(OH)CH3 for threonine; —CH2SH for cysteine; —CH2CH2SCH3 for methionine; —CH2-(phenyl) for phenylalanine; —CH2-(phenyl)-OH for tyrosine; —CH2-(indole) for tryptophan; —CH2COOH for aspartic acid; —CH2C(O)(NH2) for asparagine; —CH2CH2COOH for glutamic acid; —CH2CH2C(O)NH2 for glutamine; —CH2CH2CH2-N(H)C(NH2)NH for arginine; —CH2-(imidazolo) for histidine; —CH2(CH2)3NH2 for lysine, including the same amino acid side chains bearing suitable protecting groups. Moreover, the term "amino acid" includes the non-proteinogenic amino acids, such as ornithine (Orn), norleucine (Nle), norvaline (NVa), β-alanine, L or D α-phenylglicine (Phg), diaminopropionic acid, diaminobutyric acid, and all the others well-known to the state of the art of peptide chemistry.

In compounds of formula (I), as above described, the term "alkyl" means $C_{1-8}$ alkyl, $C_{2-8}$ alkenyl and $C_{2-8}$ alkynyl groups, which represent both linear and cyclic radicals, such as: methyl, ethyl, propyl, isopropyl, butyl, pentyl, hexyl, heptyl, octyl, ethenyl, propenyl, butenyl, isobutenyl, acetylenyl, propargyl, butynyl, etc. . . .

The term "cycloalkyl" represents: cyclopropane, cyclobutane, cyclopentane, cycloheptane, cyclooctane, norbornane, canphane, adamantane.

The term "aryl" means the phenyl, biphenyl and naphtyl groups, all optionally substituted.

The term "heterocycle" specifically represents saturated or unsaturated heterocycles containing one or more nitrogen atoms, and more specifically: pyrrole, pyrazole, pyrrolidine, imidazole, indole, pyridine, pyrimidine, pyrazine, triazole, piperidine, all optionally substituted.

Optionally substituted rings (aryls, cycloalkyls and heterocycles) are meant to be functionalized with one or more, and preferably with one or two of the types chosen among the groups consisting of: alogens, OH, nitrile, nitro, $C_{1-6}$ alkyl, $OC_{1-6}$ alkyl, NH2, $NHC_{1-6}$ alkyl, $C_{1-6}$ alkyl-Z, $OC_{1-6}$ alkyl-Z, con Z=alogen, OH, tosylate, trifluoromethanesulfonate.

The term "alogen" represents fluorine, chlorine, bromine, iodine.

DRAWING CAPTIONS

FIG. 1a. Inhibition curve of compound 38 for $\alpha v\beta 3$.
FIG. 1b. Inhibition curve of compound 38 for $\alpha v\beta 5$.
FIG. 2a. Inhibition curve of compound 48 for $\alpha v\beta 3$.
FIG. 2b. Inhibition curve of compound 48 for $\alpha v\beta 5$.
FIG. 3. Cellular adhesion inhibition assays of compounds 38 and 48 for the A375M melanoma cell line.

DETAILED DESCRIPTION OF THE INVENTION

Compounds of formula (I) according to the invention can also be represented by the following formulas (Ia)-(Ib)
where X, Y, V and W are as above described.
Preferably, compounds of formula (Ia) or (Ib) are those wherein
W—X— is chosen in the group consisting of W—(CH2)n-, where n=1,2,3;
V—Y— is chosen in the group consisting of V—(CH2)p-CH(R5)-N(R4)-CO—CH2-, V—CH2-CH(R5)-N(R4)-CO—CH2-N(R1)-CH2-, V—(CH2)p-CH(R5)-N(R4)-(CH2)m-, where m e p are independently=0,1,2; R1=H, alkyl; R4=H, Me, Ph, SO2aryl optionally substituted; R5=H, para-F-Ph, para-OH-Ph;
W is chosen in the group consisting of a guanidino group,

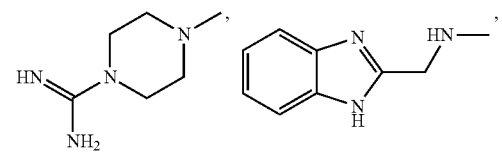

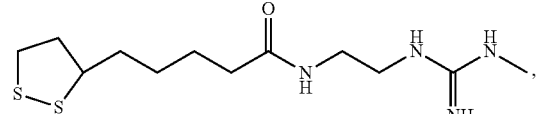

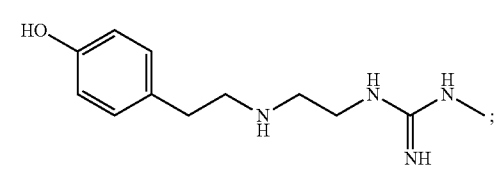

V is a COOH group or CONHOH.
Particularly preferred compounds are those of formula (Ia)

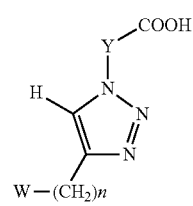

wherein
n=1,2,3;
Y—COOH is chosen in the group consisting of;

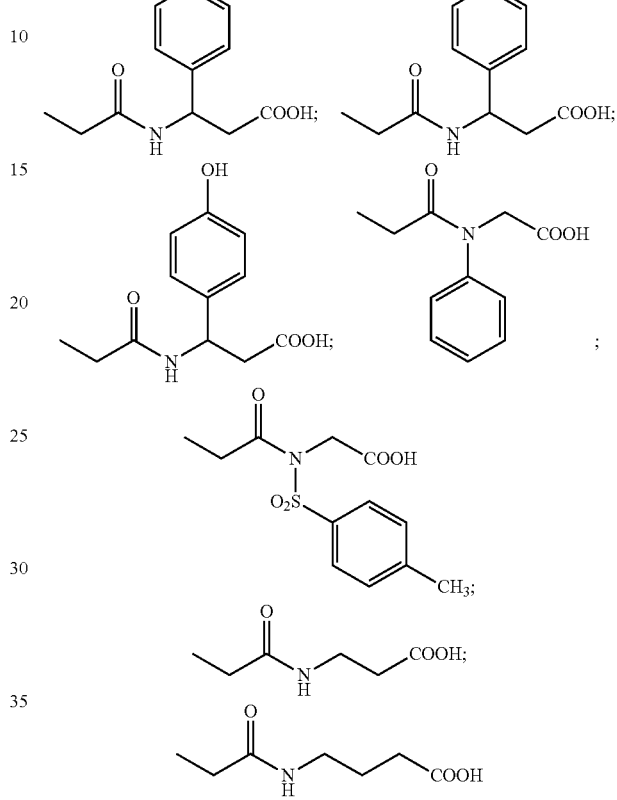

W is chosen in the group consisting of a guanidino group,

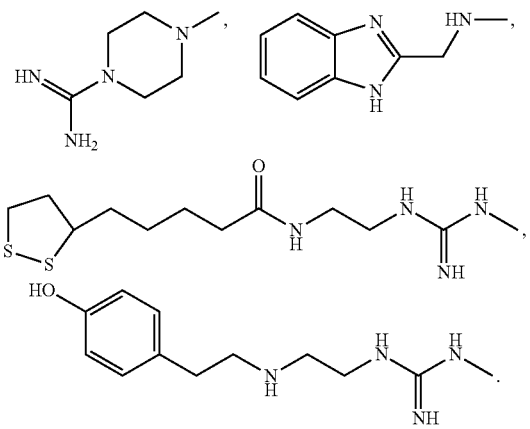

Compounds of formula (I) as above described can be obtained starting from readily obtainable precursors, also as enantiopure molecules, and specifically from the combination of two molecules bearing an azido group and a C-terminal triple bond, respectively, by means of "click-chemistry", according to Scheme 1.

Scheme 1

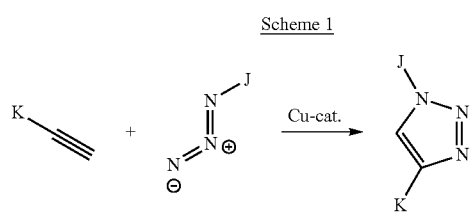

Specifically, compounds of formula (I) can be obtained through a process comprising a Huisgen 1,3-dipolar cycloaddition between azide J-N3 and alkyne K—C≡CH, catalyzed by copper with or without ascorbic acid, where J and K are precursors of Y—V and X—W groups.

Subsequent to the cycloaddition, the aforesaid process to achieve the final compounds of formula (I), as above described, consists of chemical manipulations of J and K functional groups to give Y—V and X—W groups, as above described. Thus, the possible insertion of the guanidino group or its isostere is taken into account, followed by final deprotection of COOH and guanidino groups or their isosteres. The process is general, and allows for the creation of a variable number of derivatives which show diversity either for the functional groups or for their relative position, as a function of the choice of the components for the 1,3-dipolar cycloaddition reaction and the catalyst type. In particular, by applying the process of Scheme 1, which involves the catalysis by copper salts, such as CuI, CuSO4, CuSO4 with Cu powder, Cu(OAc)2, or iodo(triethylphosphite)Cu, with or without sodium ascorbate, in water-t-butanol solvent mixture or in tetrahydrofuran, at room temperature or under microwave irradiation, it is possible to achieve 1,2,3-triazole-based molecules of formula (Ia), as above described, starting from alkyne K—C≡CH and azide J-N3, where K is a protected precursor of —X—W group, and J is a protected precursor of the —Y—V group. Alternatively 1,2,3-triazole-based molecules of formula (Ib), as above described, can be achieved starting from alkyne K—C≡CH and azide J-N3, where K is a protected precursor of the —Y—V group, and J is a protected precursor of the —X—W group.

After the cycloaddition, the process for preparing compounds of formula (I) consists of two or three synthetic steps depending on the type of the —X—W precursor. Specifically, if J or K are a direct protected derivative of the —X—W group (meaning that J or K already contain the guanidino group or its isostere), the process involves the 1,3-dipolar cycloaddition reaction, followed by removal of V and W protecting groups (see the synthesis of compounds 33-49 and 52-59). If J or K are indirect precursors of the —X—W group (meaning that J or K do not contain the guanidino group or its isostere, but a functional group suitable for subsequent introduction of the guanidino group or its isostere), the process consists of 1,3-dipolar cycloaddition reaction, followed by the introduction of the protected or free isostere, according to the definitions given for W, using the methods known in the state of the art. For example, this can be achieved by guanidinylation reaction between a derivative having -J=-X—NH2 and a free or protected guanidino group or its isostere (see the synthesis of compounds 50-51 and Scheme 7), or by means of a Mitsunobu reaction between a precursor having -J=-X—OH and a guanidino group or its isostere, followed by removal of the protecting groups of V and W.

The synthesis of compounds of formula (I) is significantly less complicated than that of the cyclic peptidomimetics known in the state of the art, and it is possible to achieve even large quantities of final products by means of significantly simple processes. Moreover, the 1,2,3-triazole nucleus is quite stable, as it is not easily hydrolyzed, oxidized or reduced, thus suggesting high in vivo resistance. The preparation of alkynes and azides is achieved according to synthetic methods known in the state of the art.

In order to provide few examples, selected compounds for the 1,3-dipolar cycloaddition reaction, as above described, are given in Table 1:

TABLE 1

Representative molecules for the preparations of selected compounds of general formula (I).

| | ALKYNE |
|---|---|
| 1 | Boc-NH-C(=N-Boc)-NH-CH2-C≡CH |
| 2 | Boc-NH-C(=N-Boc)-NH-CH2CH2-C≡CH |
| 3 | Boc-NH-C(=N-Boc)-NH-CH2CH2CH2-C≡CH |
| 4 | Boc-NH-C(=N-Boc)-N(piperazine)-CH2-C≡CH |
| 5 | Boc-NH-C(=N-Boc)-N(piperazine)-CH2CH2-C≡CH |
| 6 | MeO2C-CH(4-F-C6H4)-NH-C(=O)-CH2-N(CH3)-CH2-C≡CH |
| 7 | MeO2C-CH(4-F-C6H4)-NH-C(=O)-CH2-N(CH3)-CH2CH2-C≡CH |

TABLE 1-continued

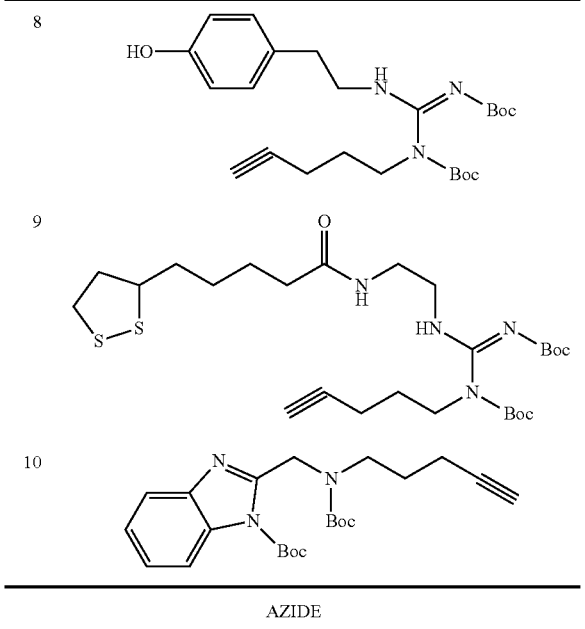

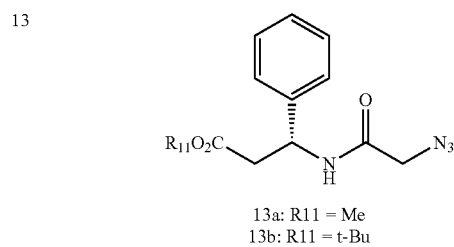

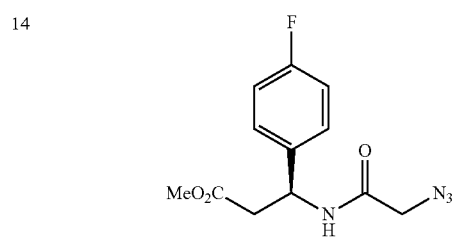

TABLE 1-continued

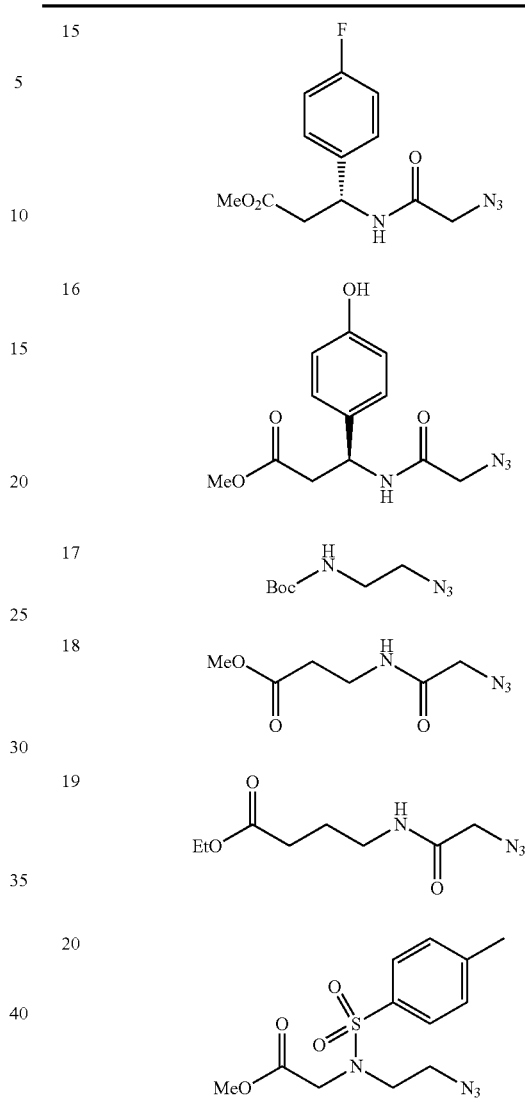

Alkyne 6 and azide 14, as reported in Table 1, are obtained starting from β-(S)-para-F-phenylalanine methyl ester as shown in Scheme 2, which in turn is obtained from the corresponding methyl para-F-cynnamate according to methods known in the state of the art (Davies, S. G.; Ichihara, O. *Tetrahedron: Asymmetry* 1991, 2, 183). The reaction between β-(S)-para-F-phenylalanine methyl ester 21 and bromoacetyl bromide in anhydrous solvent, preferably anhydrous dichloromethane, in the presence of a base, preferably triethylamine, and preferably at room temperature until reaction completion, gives the corresponding bromide derivative 22. Subsequent treatment with NaN3 in a polar aprotic anhydrous solvent, preferably DMF, at refluxing temperature until reaction completion, results in the achievement of the corresponding azide 14. The reaction between bromide 22 and N-methyl-propargylamine in a polar aprotic solvent, preferably DMF, and in the presence of a base, preferably triethylamine, at room temperature until reaction completion, gives alkyne 6. Similarly, alkyne 7 and azide 15 shown in Table 1 can be obtained starting from the corresponding β-(R)-para-F-phenylalanine methyl ester.

Scheme 2

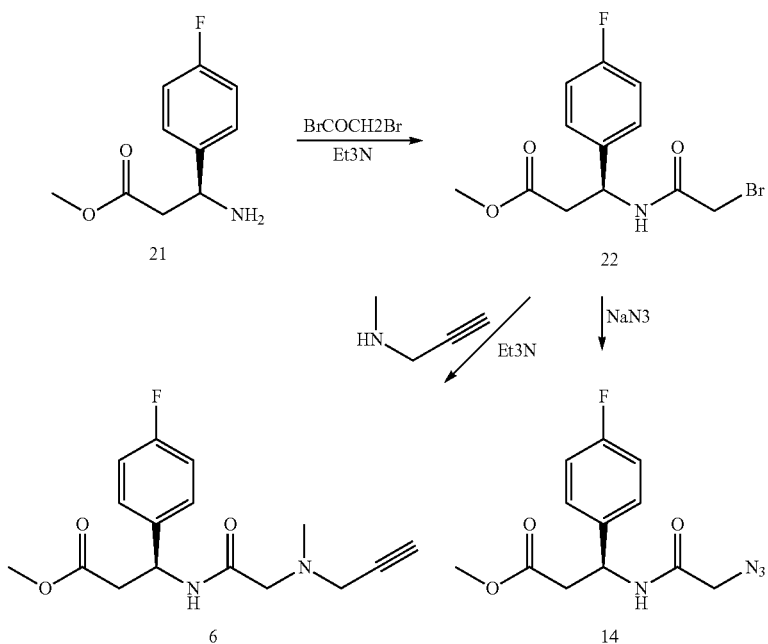

Alkynes 1-3 as reported in Table 1, can be prepared by Mitsunobu reaction from the corresponding alkynol and N,N-di-Boc-guanidine in anhydrous aprotic solvent, preferably tetrahydrofuran, under microwave irradiation, preferably at 110° C., until reaction completion. Alkyne 4 as reported in Table 1, can be obtained by SN2 reaction between compound 23 (Scheme 3) and propargyl bromide. Alkyne 5 of Table 1 can be easily obtained by treating commercially available Boc-piperazine 23 with a butynol derivative, preferably butynyl mesylate, followed by Boc removal, preferably by treatment with a 1:1 TFA-dichloromethane mixture, and final guanidinylating reaction, preferably by using di-Boc-guanidinyl triflate, according to Scheme 3.

Scheme 3

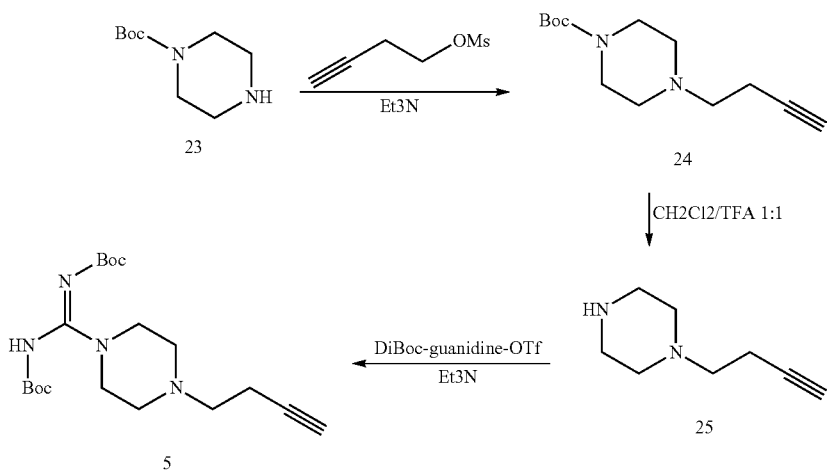

Alkynes 8 and 9 can be obtained by reacting the common precursor 27, which is achieved by Mitsunobu reaction between commercially-available di-Boc-thiourea 26 and 4-pentynol, as reported (Delle Monache, G.; Botta, B.; Delle Monache, F.; Espinal, R.; De Bonnevaux, S. C.; De Luca, C.; Botta, M.; Corelli, F.; Carmignani, M. *J. Med. Chem.* 1993, 36, 2956), with tyramine or the lipoic acid derivative 28, prepared as reported (Nam, J.; Won, N.; Jin, H.; Chung, H.; Kim, S. *J. Am. Chem. Soc.* 2009, 131, 13639), as outlined in Scheme 4.

Scheme 4

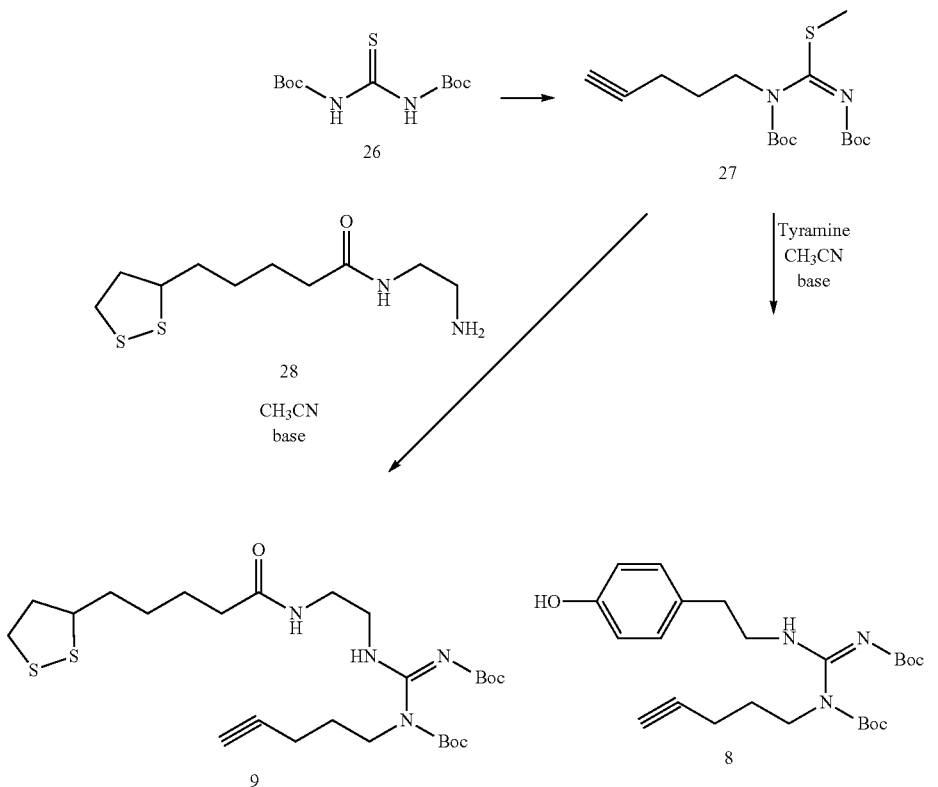

Alkyne 10 is obtained by Mitsunobu reaction between di-Boc-benzimidazole and 4-pentynol.

Azide 11 is prepared as for 14 (Scheme 2) using N-phenylglycine. Azides 12 and 13 are obtained as for 14 (Scheme 2) starting from (S)- or (R)-β-phenylalanine methyl or t-butyl esters, respectively. Azide 16 can be obtained as for 14 (Scheme 2) starting from the corresponding β-(S)-para-OTIPS-phenylalanine methyl ester, obtained from the corresponding methyl para-OTIPS-cynnamate, which in turn is obtained as reported by Maier et al. (Schmauder, A.; Sibley, L. D.; Maier, M. E. *Chem. Eur. J.* 2010, 16, 4328), according to methods known in the state of the art (Davies, S. G.; Ichihara, O. *Tetrahedron: Asymmetry* 1991, 2, 183). Azide 17 is prepared from ethanolamine as showed in Scheme 5. Amine protection of ethanolamine as Boc-derivative 29 is followed by conversion to the corresponding mesylate 30, and final conversion to azide 17 by reaction with NaN3.

Scheme 5

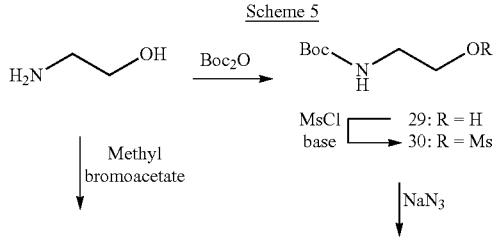

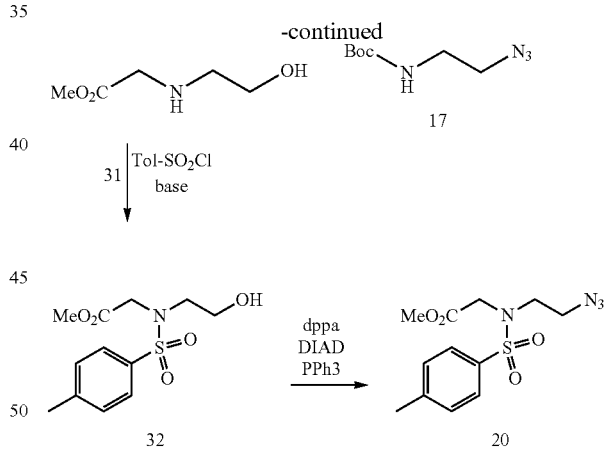

Azides 18 and 19 are prepared as for 14 (Scheme 2) using methyl 3-aminopropionate or ethyl 4-aminobutyrate, respectively. Finally, azide 20 is obtained, as reported in Scheme 5, from ethanolamine by reaction with methyl bromoacetate to give 31, which is treated with tolyl-sulfonyl chloride in the presence of a base to give 32. Compound 20 is finally obtained by conversion of 32 to azide 20 by Mitsunobu reaction with DPPA (diphenylphosphorylazide).

For example, Table 2 shows compounds of formula (Ia) and (Ib) obtained according to the above-described process, comprising the Cu-catalyzed 1,3-dipolar cycloaddition reaction between an azide and an alkyne of Table 1, followed by acid-mediated hydrolysis.

TABLE 2
Representative compounds of general formula (I).
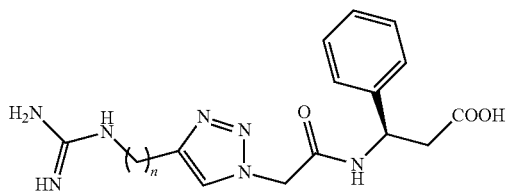
33: n = 1
34: n = 2
35: n = 3
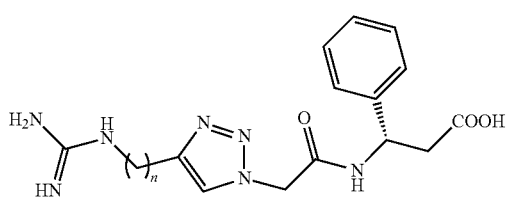
36: n = 1
37: n = 2
38: n = 3
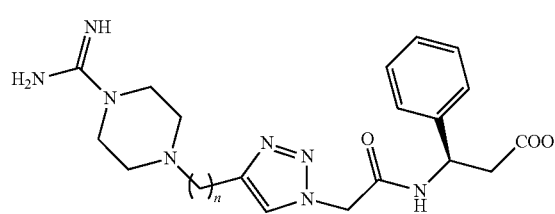
39: n = 1
40: n = 2
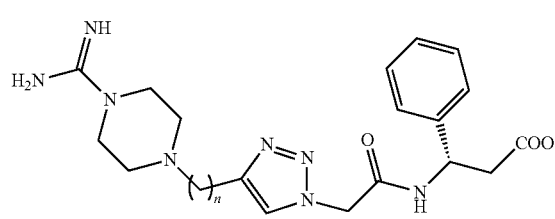
41: n = 1
42: n = 2
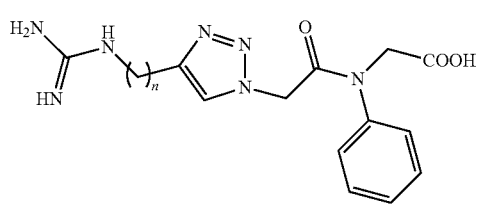
43: n = 1
44: n = 2
45: n = 3
TABLE 2-continued
Representative compounds of general formula (I).
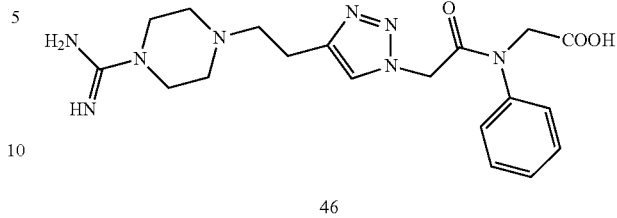
46
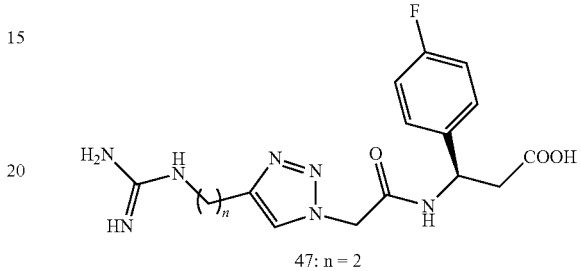
47: n = 2
48: n = 3
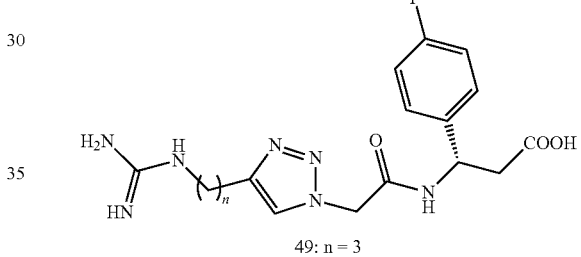
49: n = 3
50
51

TABLE 2-continued
Representative compounds of general formula (I).
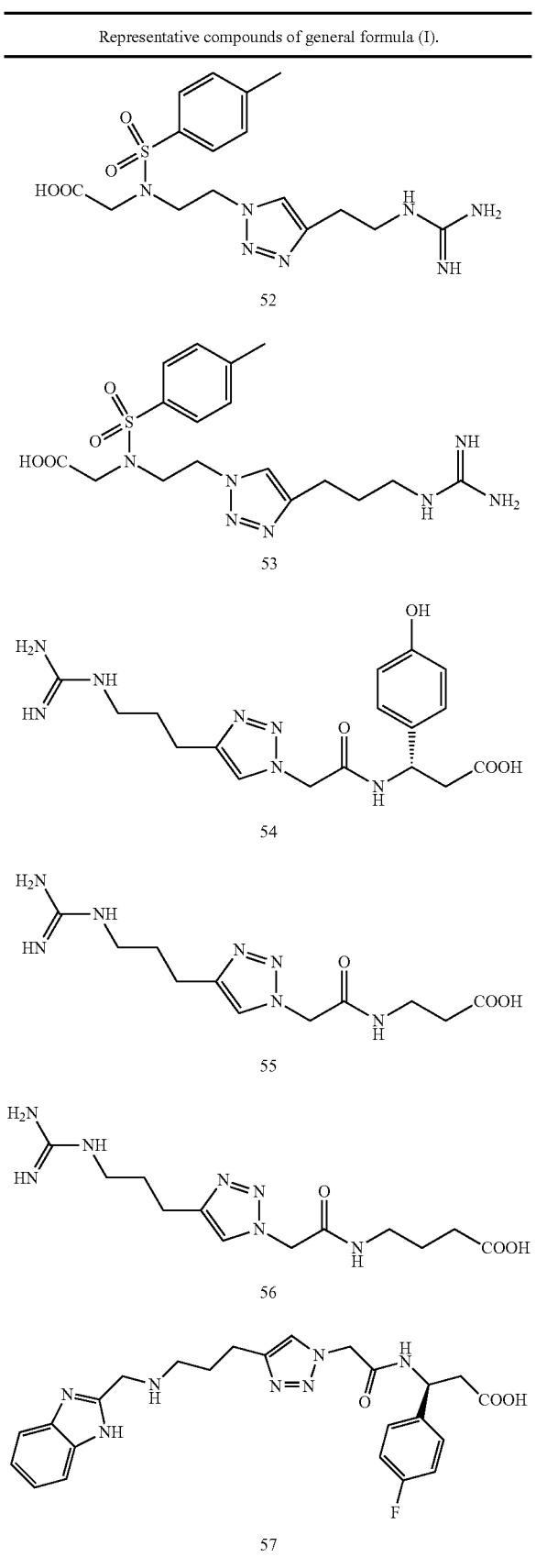
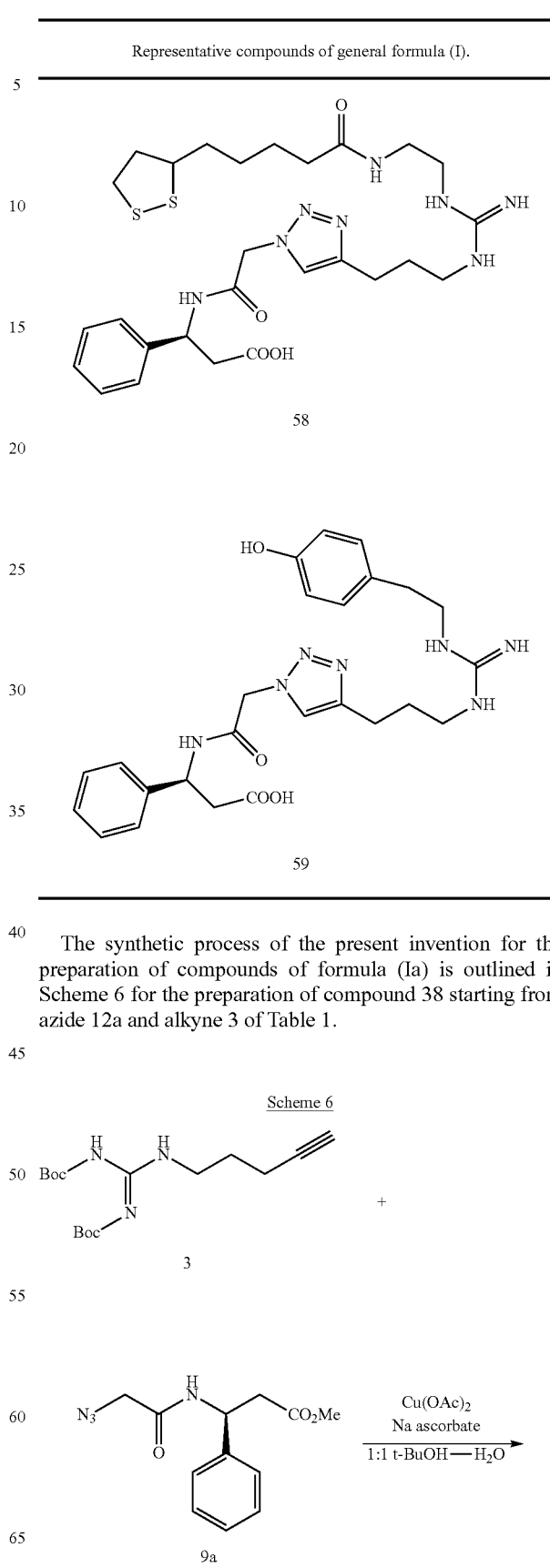
The synthetic process of the present invention for the preparation of compounds of formula (Ia) is outlined in Scheme 6 for the preparation of compound 38 starting from azide 12a and alkyne 3 of Table 1.

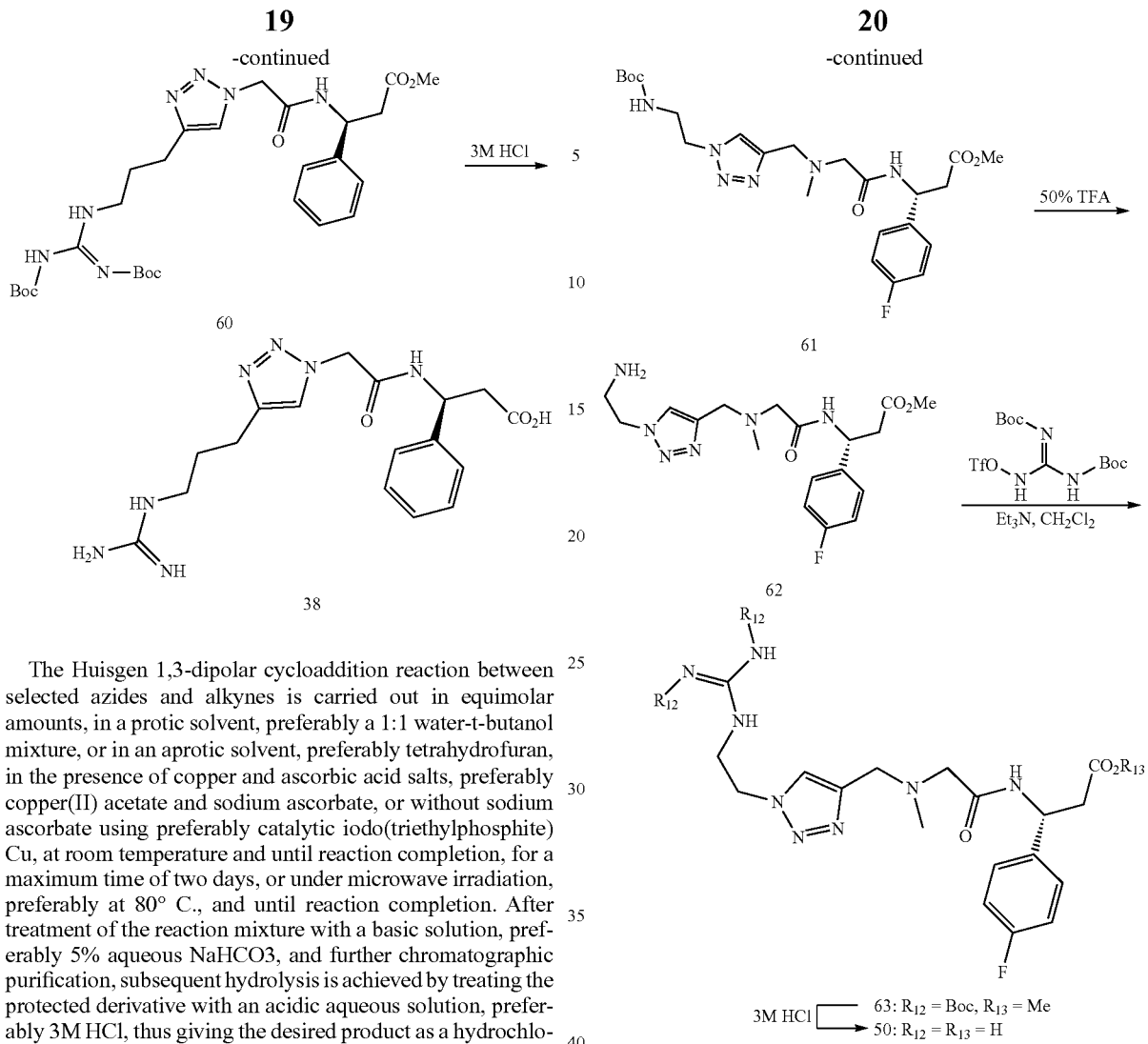

The Huisgen 1,3-dipolar cycloaddition reaction between selected azides and alkynes is carried out in equimolar amounts, in a protic solvent, preferably a 1:1 water-t-butanol mixture, or in an aprotic solvent, preferably tetrahydrofuran, in the presence of copper and ascorbic acid salts, preferably copper(II) acetate and sodium ascorbate, or without sodium ascorbate using preferably catalytic iodo(triethylphosphite) Cu, at room temperature and until reaction completion, for a maximum time of two days, or under microwave irradiation, preferably at 80° C., and until reaction completion. After treatment of the reaction mixture with a basic solution, preferably 5% aqueous NaHCO3, and further chromatographic purification, subsequent hydrolysis is achieved by treating the protected derivative with an acidic aqueous solution, preferably 3M HCl, thus giving the desired product as a hydrochloride salt after solvent evaporation.

In the case of compounds 50 and 51 of formula (Ib), the synthetic process is based on the introduction of the guanidino group subsequent to the "click chemistry" reaction. For example, the preparation of compound 50 of formula (I) consists of the Cu-catalyzed Huisgen 1,3-dipolar cycloaddition using precursors 17 and 7 of Table 1, as reported in Scheme 7. Subsequent deprotection of the adduct 61, and guanidinylation to give the protected compound 63, gives the final product 50 after acidic hydrolysis.

Scheme 7

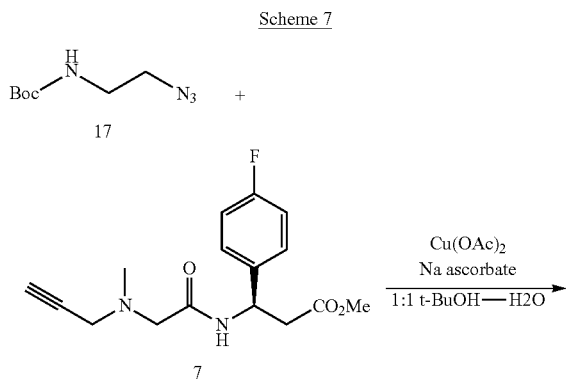

In vitro competition studies, which have been carried out using αvβ3 and αvβ5 receptors, purified from human placenta by affinity chromatography, have shown a high binding affinity of 38 for both receptors, having a IC50=16.4 nM for αvβ3 and IC50=1.02 μM for αvβ5 (FIG. 1). The introduction of a fluorine on the aromatic ring in para position, in analogy with a potential labelling with fluorine-18 (PET radioisotope), corresponding to compounds 48 and 49 of formula (I), has shown that the presence of the fluorine maintain the affinity towards the receptor, though with lowered potency of about an order of magnitude (compound 48: IC50=215 nM for αvβ3, and IC50=9.90 μM for αvβ5, as shown in FIG. 2; compound 49: IC50=101 nM for αvβ3). High binding affinity is observed for compound 55 lacking the aromatic ring (IC50=13 nM for αvβ3). Compounds 54 and 57 show inhibition towards αvβ3 with IC50=2.1 μM and 200 nM. Moreover, compound 52 displays 77% and 54% inhibition of 125I-Echistatin binding to αvβ3 at 10 μM and 1 μM concentrations, respectively. Finally, compound 59 shows inhibition towards αvβ3 with IC50=308 nM.

A series of experiments carried out using the flux cytometry technique and specific monoclonal antibodies, allowed for the setup of particular human melanoma cells characterized by an over-expression of integrin receptors. Such cells have been used to test the capability of selected compounds of formula (I) at 10, 1.0 and 0.1 μM concentrations, of inhibiting the binding between these cells and suitable substrates containing the RGD sequence, such as vitronectin, fibronectin, and osteopontin (FIG. 3). The results clearly show that compound 48 significantly inhibits the binding of melanoma cells to both vitronectin and osteopontin, whereas it displays a minor effect towards the adhesion of the cells to fibronectin. Compound 48 significantly inhibits only the binding of the cells to vitronectin, whereas it shows a minor effect towards the adhesion of the cells to both osteopontin and fibronectin. Taken all together, these data demonstrate that the RGD-like molecules of formula (I) are capable to exert important biological effects also to integrin receptors associated to the plasma-membrane of tumor cells, which is a pre-requisite for their use in-vivo. Moreover, these results show that among the two selected peptidomimetics of formula (I), compound 38 displays a higher affinity for the αvβ3 integrin receptor, which recognizes the RGD sequence exposed both on vitronectin and osteopontin.

These results suggest a potential use of compounds of formula (I), as above-described, as medicaments and/or diagnostics for the treatment and/or diagnosis of pathologies where integrins are involved. Compounds of the present invention can be used as antagonists of integrin receptors, in particular of integrins that recognize the tripeptide Arg-Gly-Asp (RGD) sequence, and more specifically, of αvβ3 and αvβ5 integrins, thus resulting useful, for example, for the treatment of initiating or growing tumors (acting as anti-angiogenic agents), osteoporosis, or rheumatoid arthritis.

Compounds of formula (I) according to the present invention, when containing one or more radioisotopes, can be applied as diagnostics, or starting from compounds of formula (I) as above-described, conjugated compounds with suitable molecular probes can be obtained.

Experimental Section

General procedure (A) for the synthesis of alkynes 1-3 of Table 1. To a solution of alkyn-1-ol (1 eq) in anhydrous THF, PPh$_3$ (1 eq) and N,N'-di-Boc-guanidine (1 eq) are added under a nitrogen atmosphere. Successively, DIAD (1 eq) is slowly added at 0° C., then, the mixture is left reacting in a microwave synthesizer at 110° C. for 30 min. The solvent is evaporated and the crude is purified by flash chromatography (1:2 EtOAc-petr. et.), thus giving pure product.

N,N'-Di-Boc-N"-(prop-2-ynyl)-guanidine (1). Compound 1 is obtained according to general procedure A in 79% yield. (1:2 EtOAc-petr. et., Rf=0.80). $^1$H NMR (CDCl$_3$, 200 MHz) δ 8.46 (br, 1H), 4.22 (dd, J=4.8, 2.6 Hz, 2H), 2.26 (t, J=2.6 Hz, 1H), 1.49 (s, 18H) ppm.

N,N'-Di-Boc-N"-(but-3-ynyl)-guanidine (2). Compound 2 is obtained according to general procedure A as a white solid in 72% yield. (1:2 EtOAc-petr. et., Rf=0.80). $^1$H NMR (CDCl$_3$, 200 MHz) δ 9.20 (br, 1H), 4.08 (t, J=7.0 Hz, 2H), 2.52 (td, J=7.0, 2.6 Hz, 2H), 1.95 (t, J=2.6 Hz, 1H), 1.53 (s, 9H), 1.48 (s, 9H) ppm; $^{13}$C NMR (CDCl$_3$, 50 MHz) δ 163.3 (s), 159.8 (s), 154.4 (s), 83.8 (s), 81.1 (s), 78.5 (s), 69.7 (d), 42.8 (t), 28.2 (q), 27.9 (q), 18.5 (t) ppm.

N,N'-Di-Boc-N"-(pent-4-ynyl)-guanidine (3). Compound 3 is obtained according to general procedure A as a white solid in 68% yield. (1:2 EtOAc-petr. et., Rf=0.63). $^1$H NMR (CDCl$_3$, 200 MHz) δ 9.30 (br, 1H), 4.00 (t, J=7.2 Hz, 2H), 2.23 (td, J=7.2, 2.2 Hz, 2H), 1.93 (t, J=2.2 Hz, 1H), 1.83 (m, 2H), 1.52 (s, 9H), 1.48 (s, 9H) ppm; $^{13}$C NMR (CDCl$_3$, 50 MHz) δ 163.7 (s), 160.5 (s), 154.8 (s), 83.8 (s), 83.7 (s), 78.7 (s), 68.5 (d), 43.9 (t), 28.3 (q), 28.0 (q), 27.5 (t), 16.0 (t) ppm.

[t-butoxycarbonylimino-(4-prop-2-ynyl-piperazin-1-y)-methyl]-carbamic acid t-butyl ester (4). To a solution of N,N'-di-Boc-N"'-trifluoromethanesulfonylguanidine (1.72 g, 4.40 mmol) in anhydrous CH$_2$Cl$_2$ (20 mL) Et$_3$N (674 μL, 4.84 mmol) and N-propargyl piperazine (600 mg, 4.84 mmol) are added. The mixture is left reacting at room temperature for 16 h, then the solvent is evaporated. The residue is taken up in EtOAc, and treated with a saturated aqueous NaHCO$_3$ solution and brine. Crude compound is purified by flash chromatography (2:1 EtOAc-petr. et., Rf=0.37) giving compound 4 as a yellow oil (1.01 g, 2.77 mmol) in 63% yield. $^1$H NMR (CDCl$_3$, 200 MHz) δ 9.61 (br, 1H), 3.44 (m, 4H), 3.16 (d, J=2.6 Hz, 2H), 2.41 (m, 4H), 2.18 (m, 1H), 1.27 (s, 9H) ppm.

[t-butoxycarbonylimino-(4-but-3-ynyl-piperazin-1-yl)-methyl]-carbamic acid t-butyl ester (5) (Scheme 3). To a solution of 23 (1.02 g, 5.47 mmol) triethylamine (762 μL, 5.47 mmol) and NaI (23 mg, 0.153 mmol) in DMSO but-3-ynyl mesylate (810 mg, 5.47 mmol) is dropwise added. The mixture is heated at 50° C. overnight, then water is added. The aqueous phase is treated with Et$_2$O, and the organic phase is washed with brine, and dried over sodium sulfate. After solvent evaporation, 4-but-3-ynyl-piperazine-1-carboxylic acid t-butyl ester (24) (1.10 g, 4.62 mmol, 84%) is obtained as a yellow oil. $^1$H NMR (CDCl$_3$, 200 MHz) δ 3.38 (t, J=4.8 Hz, 4H), 2.55 (m, 2H), 2.41-2.28 (m, 6H), 1.94 (t, J=2.6 Hz, 1H), 1.40 (s, 9H) ppm; $^{13}$C NMR (CDCl$_3$, 50 MHz) δ 154.3 (s), 82.3 (s), 79.5 (s), 69.1 (d), 56.9 (t), 52.6 (t), 43.5 (t), 28.4 (q), 16.7 (t) ppm. Compound 24 (1.10 g, 4.62 mmol) is left reacting for 16 h in the presence of a 1:1 mixture of CH$_2$Cl$_2$/TFA (2 mL/mmol). After solvent evaporation, the residue is taken up in MeOH, and eluted through a column containing Amberlyst A-21, thus giving pure 1-but-3-ynyl-piperazine (25) (606 mg, 4.39 mmol) in 95% yield. $^1$H NMR (CDCl$_3$, 200 MHz) δ 6.98 (br, 1H), 3.06-3.01 (m, 4H), 2.62-2.55 (m, 6H), 2.38-2.29 (m, 2H), 1.96 (t, J=2.6 Hz, 1H) ppm; $^{13}$C NMR (CDCl$_3$, 50 MHz) δ 82.1 (s), 69.4 (d), 56.6 (t), 50.6 (t), 44.1 (t), 16.8 (t). MS m/z 138 (M$^+$, 7), 99 (100), 70 (48), 56 (98) ppm. To a solution of N,N'-di-Boc-N"'-trifluoromethanesulfonylguanidine (1.52 g, 3.88 mmol) in anhydrous CH$_2$Cl$_2$ (18 mL) triethylamine (595 μL, 4.27 mmol) and 25 (590 mg, 4.27 mmol) are added. The mixture is left reacting for 16 h at room temperature, and then the solvent is evaporated. The residue is taken up in EtOAc and treated with a saturated aqueous NaHCO$_3$ solution and brine. Crude product is purified by flash chromatography (CH$_2$Cl$_2$-MeOH 12:1, Rf=0.50), giving pure 5 as a white solid (1.10 g, 2.25 mmol) in 58% yield. $^1$H NMR (CDCl$_3$, 200 MHz) δ 3.58 (m, 4H), 2.63-2.51 (m, 6H), 2.39-2.33 (m, 2H), 1.96 (t, J=2.6 Hz, 1H) ppm; $^{13}$C NMR (CDCl$_3$, 50 MHz) δ 154.7 (s), 151.2 (s), 115.9 (s), 85.9 (s), 82.3 (s), 69.2 (d), 56.6 (t), 52.3 (t), 46.7 (t), 28.0 (q), 27.8 (q), 16.8 (t); MS m/z 380 (M$^+$, 0.11), 160 (17), 121 (79), 57 (100) ppm.

(3S)-(2-Bromo-acetylamino)-3-(4-fluoro-phenyl)-propionic acid methyl ester [(S)-22] (Scheme 2). To a solution of compound (S)-21 (1.0 g, 5.08 mmol), prepared as reported (Davies, S. G.; Ichihara, O. *Tetrahedron: Asymmetry* 1991, 2, 183), and triethylamine (0.71 mL, 5.08 mmol) in anhydrous CH$_2$Cl$_2$ (5 mL) bromoacetyl bromide (442 μL, 5.08 mmol) is dropwise added at −10° C. After 15 min at −10° C., the mixture is allowed to reach room temperature, and it is left reacting for additional 30 min. Then, water is added and the two phases are separated. The organic phase is washed with 5% HCl and brine, and it is dried over anhydrous Na$_2$SO$_4$. After solvent evaporation, compound (S)-22 is obtained as a yellow oil (1.40 g, 4.42 mmol) in 87% yield. $^1$H NMR (CDCl$_3$, 200 MHz) δ 7.74 (br, 1H), 7.30-7.23 (m, 2H), 7.07-6.98 (m, 2H), 5.36 (dt, J=8.0, 5.6 Hz, 1H), 3.90 (s, 2H), 3.64

(s, 3H), 2.88 (dd, J$_1$=5.6, 3.8 Hz, 2H) ppm; $^{13}$C NMR (CDCl$_3$, 50 MHz) δ 171.3 (s), 164.8 (s), 162.1 (d, J$_{CF}$=245 Hz), 135.5 (s), 127.8 (d, J$_{CF}$=8.2 Hz), 115.6 (d, J$_{CF}$=20 Hz), 52.1 (q), 49.6 (d), 39.6 (t), 29.1 (t) ppm.

(3R)-(2-Bromo-acetylamino)-3-(4-fluoro-phenyl)-propionic acid methyl ester [(R)-22]. Compound (R)-22 is prepared as described for (S)-22 starting from (R)-21 (1.0 g, 5.08 mmol). After solvent evaporation, (R)-22 is obtained as a yellow oil (1.35 g, 4.27 mmol) in 84% yield and with NMR data as for (S)-22.

(S)-3-(4-Fluoro-phenyl)-3-[2-(methyl-prop-2-ynyl-amino)-acetylamino]-propionic acid methyl ester (6) (Scheme 2). A solution of compound (S)-22 (654 mg, 2.18 mmol) in DMF (2 mL) is added at room temperature to a solution of N-methyl propargylamine (181 μL, 2.18 mmol) and triethylamine (453 μL, 3.27 mmol) in DMF (5 mL). After 1 h, the mixture is brought to 80° C. and left reacting for 16 h. Then, water is added and the organic phase is extracted with diethyl ether. Crude product is purified by flash chromatography (3:2 EtOAc-petr. et., Rf=0.50) giving pure 6 as a yellow oil (0.990 g, 3.54 mmol) in 80% yield. $^1$H NMR (CDCl$_3$, 200 MHz) δ 7.81 (d, J=8.4 Hz, 1H), 7.26-7.18 (m, 5H), 5.43-5.34 (m, 1H), 3.55 (s, 3H), 3.28 (d, J=2.5 Hz, 2H), 3.05 (s, 2H), 2.81 (t, J=6.0 Hz, 2H), 2.30 (s, 3H), 2.19 (t, J=1.2 Hz, 1H) ppm; $^{13}$C NMR δ 170.9 (s), 169.2 (s), 140.4 (s), 128.5 (d), 127.4 (d), 126.1 (d), 73.5 (t), 59.3 (t), 51.6 (q), 49.0 (t), 46.2 (t), 42.2 (q), 40.2 (t) ppm.

(R)-3-(4-Fluoro-phenyl)-3-[2-(methyl-prop-2-ynyl-amino)-acetylamino]-propionic acid methyl ester (7). Compound 7 is prepared as reported for 6 starting from (R)-22, with same NMR data as for 6.

N,N'-di-Boc-1-hex-4-ynyl-2-methyl-isothiourea (27) (Scheme 4). To a solution of N,N'-diBoc-2-Methyl-isothiourea 26 (500 mg, 1.72 mmol), PPh$_3$ (540 mg, 2.05 mmol) and pent-4-yn-1-ol (145 mg, 1.72 mmol) in anhydrous THF (20 mL) DIAD (415 ml, 2.06 mmol) is dropwise added at −10° C. Then, the mixture is left reacting in a microwave synthesizer at 50° C. for 30 min. The solvent is evaporated, and the crude is purified by flash chromatography (10:1 EtOAc-petr. et., Rf=0.33), thus giving pure N,N'-diBoc-1-Hex-4-ynyl-2-methyl-isothiourea 27 in 98% yield. $^1$H NMR (CDCl$_3$, 200 MHz) δ 3.63 (t, 2H), 2.39 (s, 3H), 2.27-2.20 (m, 2H), 1.97 (t, 2H), 2.35 (t, 2H), 1.90 (t, 2H), 1.52 (s, 9H), 1.48 (s, 9H) ppm.

Alkyne 8. A solution of tyramine (200 mg, 0.637 mmol), 27 (600 mg, 1.68 mmol) and triethylamine (510 ml, 5.06 mmol) in anhydrous THF (20 mL) is left reacting in a microwave synthesizer at 100° C. for 1 h, and then the solvent is evaporated. The residue is taken up in EtOAc, and treated with brine. Crude compound is purified by flash chromatography (1:2 EtOAc-petr. et., Rf=0.42) to give compound 8 (350 mg) in 47% yield. $^1$H NMR (CDCl$_3$, 200 MHz) δ 7.04 (d, 2H), 6.77 (d, 2H), 3.66 (t, 2H), 3.42 (t, 2H), 3.42 (t, 2H), 2.18-2.04 (m, 2H), 1.95 (t, 2H), 1.62 (t, 2H), 1.49 (s, 9H), 1.46 (s, 9H).

Alkyne 9. 5-[1,2]Dithiolan-3-yl-pentanoic acid (2-amino-ethyl)-amide 28 is obtained as reported (Nam, J.; Won, N.; Jin, H.; Chung, H.; Kim, S. J. Am. Chem. Soc. 2009, 131, 13639) starting from lipoic acid (2.0 g, 9.70 mmol), 1,1-carbonyldiimidazole (200 g, 12.3 mmol), and ethylenediamine (3.5 mL, 48.4 mmol) in 80% yield. $^1$H NMR (D$_2$O, 200 MHz) δ 3.62-3.52 (m, 1H), 3.34-3.26 (m, 2H), 3.22-3.08 (m, 2H), 2.82 (t, 2H), 2.52-2.40 (m, 1H), 2.20 (t, 1H), 1.96-1.84 (m, 1H), 1.72-1.58 (m, 5H), 1.51-1.38 (m, 2H) ppm. A solution of 28 (787 mg, 3.17 mmol), 27 (754 mg, 2.11 mmol) and triethylamine (640 ml, 6.33 mmol) in anhydrous THF (30 mL) is left reacting in a microwave synthesizer at 100° C. for 1 h. Then, the solvent is evaporated. The residue is taken up in EtOAc, and treated with brine. Crude compound is purified by flash chromatography (30:1 CH$_2$Cl$_2$—CH$_3$OH, Rf=0.37) giving 9 (480 mg) in 41% yield. $^1$H NMR (CDCl$_3$, 200 MHz) δ 6.42 (br, 1H), 3.75-3.68 (m, 2H), 3.50-3.35 (m, 4H), 3.30-3.15 (m, 2H), 2.52-2.40 (m, 2H), 2.30-2.10 (m, 5H), 1.97 (t, 1H), 1.95-1.85 (m, 2H), 1.80-1.70 (m, 2H), 1.72-1.60 (m, 4H), 1.49 (s, 9H), 1.45 (s, 9H) ppm.

2-(tert-Butoxycarbonyl-pent-4-ynyl-amino)-methyl-benzoimidazole-1-carboxylic acid tert-butyl ester (10). To a solution of C-(1H-benzoimidazol-2-yl)-methylamine (200 mg, 1.0 mmol) and triethylamine (139 μL, 1 mmol) in CH$_2$Cl$_2$ (5 mL) (Boc)$_2$O (420 mg, 2 mmol) is added, and the reaction mixture is stirred at r.t. for 1 h. After solvent evaporation, the crude product is purified by flash chromatography (1:1 EtOAc-Et.petr., Rf=0.5), to give 2-(tert-butoxycarbonylamino-methyl)-benzoimidazole-1-carboxylic acid t-butyl ester as a yellow oil (246 mg, 0.71 mmol) in 71.% yield. $^1$H NMR (CDCl$_3$, 200 MHz) є 7.96-7.91 (m, 1H), 7.72-7.67 (m, 1H), 7.35-7.26 (m, 2H), 5.85 (br, 1H), 4.80 (d, 2H), 1.71 (s, 9H), 1.48 (s, 9H) ppm. This intermediate (175 mg, 0.5 mmol) is dissolved in anhydrous THF (10 mL) and PPh$_3$ (330 mg, 0.5 mmol) and 4-pentynol (46 μL, 0.5 mmol) are added. Then, after cooling to 0° C., DIAD (100 μL, 0.5 mmol) is slowly added, and after 15 min at 0° C., the mixture is heated under microwave irradiation at 110° C. for 1 h. Following flash chromatography purification (5:1 EtOAc-petr. et.), compound 10 is obtained in 64% yield. $^1$H NMR (CDCl$_3$, 200 MHz) δ 7.95-7.90 (m, 1H), 7.71-7.67 (m, 1H), 7.34-7.26 (m, 2H), 5.79 (d, 2H), 2.30-2.20 (m, 2H), 2.03 (s, 1H), 1.95-1.92 (m, 2H), 1.80 (t, 2H), 1.71 (s, 9H), 1.47 (s, 9H) ppm.

[(2-Azido-acetyl)-phenyl-amino]-acetic acid t-butyl ester (11). To a solution of N-phenyl-glycine methyl ester (1.65 g, 7.98 mmol) and triethylamine (1.11 mL, 7.98 mmol) in anhydrous CH$_2$Cl$_2$ (8 mL) bromoacetyl bromide (695 μL, 7.98 mmol) is dropwise added at −10° C. After 15 min at −10° C., the mixture is allowed to reach room temperature, and it is left reacting for additional 30 min. Then, water is added and the two phases are separated. The organic phase is washed with 5% HCl and brine, and it is dried over anhydrous Na$_2$SO$_4$. After solvent evaporation, 2.10 g of the corresponding bromoacetyl-derivative are obtained as a brown oil (85%). $^1$H NMR (CDCl$_3$, 200 MHz) δ 7.41 (m, 5H), 4.23 (s, 2H), 3.67 (s, 2H), 1.42 (s, 9H) ppm. To a solution of this compound (2.10 g, 6.76 mmol) in DMF, NaN$_3$ (1.32 g, 20.3 mmol) is added at room temperature. After 5 min, the mixture is brought to 80° C. and left reacting for 16 h. Then, water is added and the organic phase is extracted with diethyl ether. Crude product is purified by flash chromatography (1:3 EtOAc-petr. et., Rf=0.57), thus giving 11 as a white solid (1.06 g, 3.65 mmol) in 54% yield. $^1$H NMR (CDCl$_3$, 200 MHz) δ 7.41-7.35 (m, 5H), 4.29 (s, 2H), 3.66 (s, 2H), 1.46 (s, 9H) ppm; $^{13}$C NMR (CDCl$_3$, 50 MHz) δ 167.4 (s), 167.3 (s), 140.9 (s), 129.9 (d), 128.8 (d), 127.7 (d), 82.1 (s), 52.2 (t), 50.6 (t), 28.1 (q) ppm; MS m/z 290 (M$^+$, 0.2), 262 (0.7), 217 (11), 189 (1.8), 161 (7.3), 106 (30), 77 (18), 57 (100).

(3S)-(2-Azido-acetylamino)-3-phenyl-propionic acid methyl ester (12a) Compound 12a is prepared as described for 14, starting from (S)-β-phenylalanine methyl ester (1.0 g, 5.59 mmol), prepared as reported (Davies, S. G.; Ichihara, O. Tetrahedron: Asymmetry 1991, 2, 183). After solvent evaporation, the intermediate bromoacetyl-derivative is obtained as a brown oil (1.37 g, 4.97 mmol) in 89% yield. $^1$H NMR (CDCl$_3$, 200 MHz) δ 7.72 (d, J=8 Hz, 1H), 7.37-7.24 (m, 5H), 5.38 (dt, J=8.0, 5.8 Hz, 1H), 3.87 (s, 2H), 3.62 (s, 3H), 2.90 (t, J=5.8 Hz, 2H) ppm; $^{13}$C NMR (CDCl$_3$, 50 MHz) δ 171.1 (s), 164.9 (s), 139.6 (s), 128.6 (d), 127.6 (d), 126.0 (d), 51.8 (q), 50.1 (d), 39.5 (t), 28.9 (t) ppm. To a solution of this compound (1.37 g, 4.97 mmol) in DMF NaN$_3$ (969 mg, 14.9 mmol) is added at room temperature. After 5 min, the mixture is brought to 80° C. and left reacting for 16 h. Then, water is added and the organic phase is extracted with diethyl ether. Crude product is purified by flash chromatography (1:1 EtOAc-petr. et., Rf=0.40), giving 12a as a white solid (1.01 g, 4.12 mmol) in 83% yield. $[\alpha]^{23}{}_D$ −25.9 (c 1.8, CHCl$_3$). $^1$H NMR (CDCl$_3$, 200 MHz) δ 7.35-7.26 (m, 5H), 5.43 (dt, J=8.0, 5.8 Hz, 1H), 4.03 (s, 2H), 3.64 (s, 3H), 2.90 (t, J=5.8 Hz, 2H) ppm; $^{13}$C NMR (CDCl$_3$, 50 MHz) δ 171.2 (s), 165.9 (s), 139.7 (s), 128.7 (d), 127.4 (d), 126.1 (d), 52.5 (t), 51.9 (q), 49.5 (d), 39.6 (t) ppm.

(3S)-(2-Azido-acetylamino)-3-phenyl-propionic acid t-butyl ester (12b). Compound 12b is prepared as reported for 12a starting from (S)-β-phenylalanine t-butyl ester. $^1$H NMR (CDCl$_3$, 200 MHz) δ 7.47 (d, J=7.8 Hz, 1H), 7.32 (m, 5H), 5.39 (dt, J=8.4, 5.8 Hz, 1H), 4.02 (s, 2H), 2.80 (pseudo t, J=6.2 Hz, 2H), 1.34 (s, 9H) ppm. $[\alpha]^{23}{}_D$ −18.9 (c 1.0, CHCl$_3$).

(3R)-(2-Azido-acetylamino)-3-phenyl-propionic acid methyl ester (13a). Compound 13a is prepared as reported for 12a starting from (R)-β-phenylalanine methyl ester (1.0 g, 5.59 mmol). After solvent evaporation, the intermediate bromoacetyl-derivative is obtained as a brown oil in 85% yield. $^1$H NMR (CDCl$_3$, 200 MHz) δ 7.72 (d, J=8.0 Hz, 1H), 7.37-7.24 (m, 5H), 5.38 (dt, J=8.0, 5.8 Hz, 1H), 3.87 (s, 2H), 3.62 (s, 3H), 2.90 (t, J=5.8 Hz, 2H) ppm; $^{13}$C NMR (CDCl$_3$, 50 MHz) δ 171.1 (s), 164.9 (s), 139.6 (s), 128.6 (d), 127.6 (d), 126.0 (d), 51.8 (q), 50.1 (d), 39.5 (t), 28.9 (t) ppm. Compound 13a is obtained from this intermediate compound (1.31 g, 4.75 mmol) as reported for 12a in 80% yield and with same NMR data as reported for 12a. $[\alpha]^{23}{}_D$ +25.0 (c 1.6, CHCl$_3$).

(3R)-(2-Azido-acetylamino)-3-phenyl-propionic acid t-butyl ester (13b). Compound 13b is prepared as reported for 12a starting from (R)-β-phenylalanine t-butyl ester, with same NMR data as reported for 13b. $[\alpha]^{23}{}_D$ +18.3 (c 1.0, CHCl$_3$).

(3S)-(2-Azido-acetylamino)-3-(4-fluoro-phenyl)-propionic acid methyl ester (14) (Scheme 2). To a solution of (S)-22 (1.40 g, 4.42 mmol) in DMF NaN$_3$ (862 mg, 13.3 mmol) is added at room temperature. After 5 min, the mixture is brought to 80° C. and left reacting for 16 h. Then, water is added and the organic phase is extracted with diethyl ether. Crude product is purified by flash chromatography (3:2 EtOAc-petr. et., Rf=0.50), giving pure 14 as a yellow oil (0.990 g, 3.54 mmol) in 80% yield. $^1$H NMR (CDCl$_3$, 200 MHz) δ 7.46 (d, J=8.0 Hz 1H), 7.29-7.22 (m, 2H), 7.00 (td, J$_{HF}$=8.8 Hz, J$_{HH}$=1.4 Hz, 2H), 5.36 (dt, J=8.0, 5.6 Hz, 1H), 3.97 (s, 2H), 3.62 (s, 3H), 2.88 (pseudo t, J=5.6 Hz, 2H) ppm; $^{13}$C NMR (CDCl$_3$, 50 MHz) δ 170.9 (s), 165.7 (s), 161.9 (d, J$_{CF}$=245 Hz), 135.6 (s), 127.8 (d, J$_{CF}$=8.2 Hz), 115.5 (d, J$_{CF}$=20 Hz), 52.5 (t), 51.9 (q), 48.9 (d), 39.7 (t) ppm. $[\alpha]^{23}{}_D$ −22.0 (c 0.6, CHCl$_3$).

(3R)-(2-Azido-acetylamino)-3-(4-fluoro-phenyl)-propionic methyl ester (15). Compound 15 is prepared as reported for 14 starting from (R)-22 (1.35 g, 4.27 mmol). Crude product is purified by flash chromatography (3:2 EtOAc-petr. et., Rf=0.50), giving 15 as a yellow oil (0.932 g, 3.33 mmol) in 78% yield with same NMR data as reported for 14. $[\alpha]^{23}{}_D$ +23.4 (c 0.5, CHCl$_3$).

(3S)-(2-Azido-acetylamino)-3-(4-hydroxy-phenyl)-propionic acid methyl ester (16). Compound 16 is prepared as described for 14, starting from (R)-β-tyrosine methyl ester (1.12 g, 5.28 mmol), prepared according to literature (Davies, S. G.; Ichihara, O. Tetrahedron: Asymmetry 1991, 2, 183) from 3-(4-triisopropylsilanyloxy-phenyl)-acrylic acid methyl ester (1.0 g, 3.34 mmol), prepared as reported (Schmauder, A.; Sibley, L. D.; Maier, M. E. Chem. Eur. J. 2010, 16, 4328). After solvent evaporation, the intermediate bromoacetyl-derivative is obtained as a brown oil (0.80 g, 1.69 mmol) in 51% yield. $^1$H NMR (CDCl$_3$, 200 MHz) δ 7.61 (d, 1H), 7.20 (d, J=8.7, 2H), 6.82 (d, J=8.7, 2H), 5.32 (m, 1H), 3.91 (s, 2H), 3.61 (s, 3H), 2.98-2.78 (m, 2H), 1.37-1.15 (m, 3H), 1.07 (d, 18H) ppm. To a solution of this compound (0.80 g, 1.69 mmol) in DMF NaN$_3$ (0.33 mg, 5.07 mmol) is added at room temperature. After 5 min, the mixture is brought to 80° C., and left reacting for 16 h. Then, water is added and the organic phase is extracted with diethyl ether. Crude product is purified by flash chromatography (1:1 EtOAc-petr. et., Rf=0.40), giving 16 as a white solid (0.25 g, 0.90 mmol) in 53% yield. $^1$H NMR (CDCl$_3$, 200 MHz) δ 7.42 (d, 1H), 7.10 (d, J=8.4, 2H), 6.71 (d, J=8.4, 2H), 6.00 (br, 1H), 5.33 (m, 1H), 4.02 (s, 2H), 3.64 (s, 3H), 2.98-2.79 (m, 2H) ppm.

(2-Azido-ethyl)-carbamic acid t-butyl ester (17) (Scheme 5). A solution of ethanolamine (300 μL, 4.9 mmol) in CH$_3$CN (25 mL) is treated with (Boc)$_2$O (1.2 g, 5.5 mmol) and DMAP (120 mg, 0.98 mmol) at room temperature for 3 h. Then, the mixture is treated with 5% KHSO$_4$ and brine, and dried over sodium sulfate. After solvent evaporation, pure Boc-ethanolamine 29 is obtained in 53% yield. $^1$H NMR (CDCl$_3$, 200 MHz) δ 5.27 (br, 1H), 3.67 (br, 1H), 3.53 (t, J=5.1 Hz, 2H), 3.17-3.09 (m, 2H), 1.35 (s, 9H) ppm. This intermediate compound is dissolved in anhydrous CH$_2$Cl$_2$ and Et$_3$N (1.1 mL, 7.9 mmol) is added under a nitrogen atmosphere. The mixture is cooled to 0° C., MsCl (614 μL, 7.94 mmol) is dropwise added, and the mixture is left reacting at the same temperature for 20 min. Successively, 1M NaOH (10 mL) is added and the organic phase is separated. The mixture is treated with a saturated aqueous NaHCO$_3$ solution and with brine, and dried over sodium sulfate. After solvent evaporation, pure Boc-aminoethyl mesylate 30 (509 mg) is obtained in 64% yield. $^1$H NMR (CDCl$_3$, 200 MHz) δ 5.05 (br, 1H), 4.33-4.20 (m, 2H), 3.45-3.21 (m, 2H), 3.01 (s, 3H), 1.39 (s, 9H) ppm. The resulting mesylate 30 is dissolved in DMF (5 mL), and NaN$_3$ (413 mg, 6.36 mmol) is added at 0° C. The mixture is heated at 80° C. for 16 h, then water is added (50 mL). The organic phase is extracted with Et$_2$O (25 mL×5), and dried over sodium sulfate. After solvent evaporation, the crude product is purified by flash chromatography (1:3 EtOAc-petr. et., Rf=0.75), giving 17 (224 mg) as an oil in 61% yield. $^1$H NMR (CDCl$_3$, 200 MHz) δ 4.92 (br, 1H), 3.40-3.35 (m, 2H), 3.30-3.22 (m, 2H), 1.41 (s, 9H) ppm.

3-(2-Azido-acetylamino)-propionic acid methyl ester (18). To a solution of methyl 3-aminopropionate ester hydrochloride (1.12 g, 8.00 mmol) and triethylamine (2.2 mL (16.00 mmol) in anhydrous CH$_2$Cl$_2$ (30 mL) bromoacetyl bromide (690 μL, 8.00 mmol) is dropwise added at −10° C. After 15 min at −10° C., the mixture is allowed to reach room temperature, and is left reacting for additional 30 min. The organic phase is washed with 4M HCl, saturated Na$_2$CO$_3$ solution, and brine, and it is dried over anhydrous Na$_2$SO$_4$. After solvent evaporation, 1.02 g (4.57 mmol) of the corresponding bromoacetyl-derivative is obtained as a brown oil (57%). $^1$H NMR (CDCl$_3$, 200 MHz) δ 7.10 (br, 1H), 3.83 (s, H), 3.75 (s, 3H), 3.57 (q, 2H), 2.57 (t, 2H) ppm. $^{13}$C NMR (CDCl$_3$, 50 MHz) δ 172.7 (s), 165.4 (s), 51.9 (t), 35.5 (t), 33.4 (t), 29.1 (q) ppm. To a solution of this compound (1.02 g, 4.57 mmol) in anhydrous DMF (12 mL) NaN$_3$ (900 mg, 13.71 mmol) is added. The mixture is heated at 80° C. for 16 h. Then, water (50 mL) is added and the organic phase is extracted with diethyl ether. Crude product is purified by flash chromatography (1:1 EtOAc-Et.petr., Rf=0.4) to give 18 as a white solid (340 mg, 1.82 mmol) in 40% yield. $^1$H NMR (CDCl$_3$, 200 MHz) δ 6.91 (br, 1H), 3.94 (s, 3H), 3.68 (s, 3H), 3.53 (q, 2H), 2.55 (t, 2H) ppm. $^{13}$C NMR (CDCl$_3$, 50 MHz) δ 172.5 (s), 165.5 (s), 52.7 (t), 52.0 (t), 34.9 (t), 33.7 (q) ppm.

4-(2-Azido-acetylamino)-butyric acid ethyl ester (19). Compound 19 is prepared as described for 18. Specifically, starting from ethyl 4-aminobutanoate hydrochloride (1.00 g, 7.65 mmol), triethylamine (2.1 mL, 15.30 mmol) in anhydrous $CH_2Cl_2$ (26 mL) and bromoacetyl bromide (520 µL, 7.65 mmol), the corresponding bromoacetyl-derivative is obtained as a brown oil (59%). $^1$H NMR ($CDCl_3$, 200 MHz) δ 6.77 (br, 1H), 4.11 (q, 2H), 3.84 (s, 2H), 3.32 (m, 2H), 2.35 (t, 2H), 1.94-1.78 (m, 2H), 1.23 (t, 3H) ppm. $^{13}$C NMR ($CDCl_3$, 50 MHz) δ 172.9 (s), 165.5 (s), 60.7 (t), 39.8 (t), 31.7 (t), 29.2 (t), 24.48 (t), 14.4 (q) ppm. Starting from a solution of this compound (950 mg, 3.77 mmol) in anhydrous DMF (7 mL) and $NaN_3$ (720 mg, 11.31 mmol), after purification by flash chromatography (1:1 EtOAc-Et.petr., Rf=0.7), 19 is obtained as a white solid (350 mg, 1.64 mmol) in 44% yield. $^1$H NMR ($CDCl_3$, 200 MHz) δ 6.60 (br, 1H), 4.13 (q, 2H), 3.96 (s, 2H), 3.33 (m, 2H), 2.35 (t, 2H), 1.93-1.82 (m, 2H), 1.24 (t, 3H). $^{13}$C NMR ($CDCl_3$, 50 MHz) δ 173.0.99 (s), 166.5 (s), 60.7 (t), 52.8 (t), 39.1 (t), 31.8 (t), 24.5 (t), 14.3 (q).

[(2-Azido-ethyl)-(toluene-4-sulfonyl)-amino]-acetic acid ethyl ester (20) (Scheme 5). To a solution of (2-hydroxyethylamino)-acetic acid ethyl ester 31 (2.8 g, 10 mmol), prepared as reported (Yoon U. C.; Kwon H. C.; Hyung T. G.; Choi K. H.; Oh S. W.; Yang S.; Zhao Z.; Mariano P. S. *J. Am. Chem. Soc.* 2004, 126, 1110) and triethylamine (3.95 mL, 15 mmol) in anhydrous THF (230 mL) tosyl chloride (3.63 g, 10 mmol) is dropwise added at 0° C., and the mixture is left reacting for 4 h at 0° C. Then, water and 1N HCl are added up to pH=2. The organic phase is extracted with EtOAc. Crude compound is purified by flash chromatography (1:1 EtOAc-petr. et., Rf=0.45) giving compound 32 (3.50 g) in 56% yield. $^1$H NMR ($CDCl_3$, 200 MHz) δ 7.73 (d, 2H), 7.31 (d, 2H), 4.18 (q, 2H), 4.04 (s, 2H), 3.73 (t, 2H), 3.34 (t, 2H), 2.43 (s, 21H), 1.26 (t, 3H) ppm. To a solution of 31 (2.96 g, 9.8 mmol), $PPh_3$ (7.71 g, 29.4 mmol) in anhydrous THF (35 mL) a solution of DIAD (5.12 g, 29.9 mmol) and DPPA (8.09 g, 29.9 mmol) in anhydrous THF (10 mL) is dropwise added at −10° C. The mixture is left reacting at r.t. for 2 h. Then, a solution of 1N KOH is added, and the organic phase is extracted with EtOAc. Crude compound is purified by flash chromatography (1:3 EtOAc-petr. et., Rf=0.34), giving compound 20 (0.800 g) in 25% yield. $^1$H NMR ($CDCl_3$, 200 MHz) δ 7.72 (d, 2H), 7.31 (d, 2H), 4.15 (s, 2H), 4.09 (q, 2H), 3.56 (t, 2H), 3.39 (t, 2H), 2.43 (s, 21H), 1.21 (t, 3H) ppm.

General procedure (B) for the Cu-catalyzed cycloaddition: to a solution of alkyne (1 eq.) and azide (1 eq.) in $H_2O$/t-BuOH 1:1 (4 mL/mmol) a 0.9M sodium ascorbate solution (1 eq) and a 0.3M $Cu(OAc)_2$ solution (1 eq.) are added under a nitrogen atmosphere. The reaction mixture is left under stirring at room temperature for two days. The organic phase is extracted with $CH_2Cl_2$, treated with 5% $NaHCO_3$ and brine, and dried over sodium sulfate. After solvent evaporation, the crude product is purified by flash chromatography.

General procedure (C) for the Cu-catalyzed cycloaddition: to a solution of alkyne (1 eq.) and azide (1.2 eq.) in dry THF (6 mL/mmol) and iodo(triethylphosphite)Cu (0.1 eq.) are added under a nitrogen atmosphere. The reaction mixture is left reacting under microwave irradiation at 80° C. for 25 min. After solvent evaporation, the crude product is purified by flash chromatography.

Compound 33. Following the general procedure B, alkyne 1 (195 mg, 0.66 mmol) and azide 13b (200 mg, 0.66 mmol) in 1:1 $H_2O$/t-BuOH (2.6 mL) give, after work-up and chromatographic purification (1:1 EtOAc-petr. et., Rf=0.25), protected adduct (388 mg, 64%), precursor of 33 as a yellow oil. $^1$H NMR ($CDCl_3$, 200 MHz) δ 11.39 (br, 1H), 8.71 (br, 1H), 7.72 (s, 1H), 7.48 (br, 1H), 7.19 (m, 5H), 5.32 (m, 1H), 4.98 (s, 2H), 4.64 (s, 2H), 2.69 (m, 2H), 1.45 (s, 9H), 1.41 (s, 9H), 1.20 (s, 9H) ppm; $^{13}$C NMR ($CDCl_3$, 50 MHz) δ 169.8 (s), 164.1 (s), 163.1 (s), 155.8 (s), 152.8 (s), 144.3 (s), 139.7 (s), 128.5 (d), 127.6 (d), 126.1 (d), 123.8 (d), 83.1 (s), 81.4 (s), 79.3 (s), 52.8 (t), 50.2 (d), 41.0 (t), 36.3 (t), 28.2 (q), 27.9 (q), 27.8 (q) ppm. Compound 33 is obtained after treatment with 3M HCl (5 mL) for 16 h at room temperature, followed by solvent evaporation. $[\alpha]^{24}_D$+73.2 (c 0.2, $H_2O$). $^1$H NMR ($D_2O$, 400 MHz) δ 8.00 (s, 1H), 7.46-7.37 (m, 5H), 5.35-5.23 (m, 3H), 4.56 (s, 2H), 2.79 (m, 2H) ppm.

Compound 34. Following the general procedure B, alkyne 2 (200 mg, 0.64 mmol) and azide 13a (168 mg, 0.64 mmol) in 1:1 $H_2O$/t-BuOH (2.6 mL) give, after work-up and chromatographic purification (EtOAc-petr. et. 4:1, $R_f$=0.50), protected adduct (177 mg, 48%), precursor of 34, as a yellow oil. $^1$H NMR ($CDCl_3$, 200 MHz) δ 9.24 (br, 1H), 7.68 (s, 1H), 7.30-7.17 (m, 5H), 5.38 (m, 1H), 5.02 (s, 2H), 4.17 (m, 2H), 3.58 (s, 3H), 3.06 (m, 2H), 2.81 (m, 2H), 1.48 (s, 9H), 1.47 (s, 9H) ppm; $^{13}$C NMR ($CDCl_3$, 50 MHz) δ 170.7 (s), 164.3 (s), 163.5 (s), 160.0 (s), 154.5 (s), 145.6 (s), 139.5 (s), 128.6 (d), 127.7 (d), 125.9 (d), 123.3 (d), 84.0 (s), 78.7 (s), 52.9 (t), 51.9 (q), 50.1 (d), 44.2 (t), 39.7 (t), 28.5 (q), 28.0 (q), 25.4 (t) ppm. Compound 34 is obtained after treatment with 3M HCl (5 mL) for 16 h at room temperature, followed by solvent evaporation. $[\alpha]^{24}_D$+60.9 (c 0.3, $H_2O$). $^1$H NMR ($D_2O$, 400 MHz) δ 7.87 (s, 1H), 7.49-7.40 (m, 5H), 5.34 (m, 1H), 5.28 (d, J=5.2 Hz, 2H), 3.53 (t, J=6.4 Hz, 2H), 3.05-3.00 (m, 4H) ppm.

Compound 35. Following the general procedure B, alkyne 3 (153 mg, 0.47 mmol) and azide 13a (124 mg, 0.47 mmol) in 1:1 $H_2O$/t-BuOH (2 mL) give, after work-up and chromatographic purification (EtOAc-petr. et. 4:1, Rf=0.38), protected adduct (153 mg, 55%), precursor of 35. $^1$H NMR ($CDCl_3$, 200 MHz) δ 9.34 (br, 1H), 7.28-7.20 (m, 6H), 5.38 (m, 1H), 5.05 (s, 2H), 3.90 (m, 2H), 3.55 (s, 3H), 2.79 (m, 4H), 1.98 (m, 2H), 1.49 (s, 9H), 1.46 (s, 9H) ppm; $^{13}$C NMR ($CDCl_3$, 50 MHz) δ 170.6 (s), 164.5 (s), 163.3 (s), 159.8 (s), 154.6 (s), 147.7 (s), 139.6 (s), 128.5 (d), 127.5 (d), 126.0 (d), 122.8 (d), 83.8 (s), 78.8 (s), 52.7 (t), 51.8 (q), 50.0 (d), 43.9 (t), 39.8 (t), 28.3 (q), 28.0 (q), 27.7 (t), 22.9 (t) ppm. Compound 35 is obtained after treatment with 3M HCl (5 mL) for 16 h at room temperature, followed by solvent evaporation. $[\alpha]^{24}_D$+56.9 (c 0.4, $H_2O$). $^1$H NMR ($D_2O$, 400 MHz) δ 7.83 (s, 1H), 7.48-7.39 (m, 5H), 5.33 (pt, J=7.2 Hz, 1H), 5.26 (d, J=3.6 Hz, 2H), 3.21 (t, J=6.8, 2H), 3.00 (d, J=7.2 Hz, 2H), 2.82 (t, J=7.6 Hz, 2H), 1.97 (m, 2H) ppm.

Compound 36. Following the general procedure B, alkyne 1 (301 mg, 1.01 mmol) and azide 12b (308 mg, 1.01 mmol) in 1:1 $H_2O$/t-BuOH (4 mL) give, after work-up and chromatographic purification (1:1 EtOAc-petr. et., $R_f$=0.25), protected adduct (273 mg, 45%), precursor of 36, as a yellow oil with same NMR data as for protected 33. Compound 36 is obtained after treatment with 3M HCl (5 mL) for 16 h at room temperature, followed by solvent evaporation with same NMR data as for 33. $[\alpha]^{24}_D$−66.3 (c 0.2, $H_2O$).

Compound 37. Following the general procedure B, alkyne 2 (140 mg, 0.45 mmol) and azide 12a (118 mg, 0.45 mmol) in 1:1 $H_2O$/t-BuOH (2 mL) give, after work-up and chromatographic purification (4:1 EtOAc-petr. et., Rf=0.50), protected adduct (203 mg, 55%), precursor of 37, as a yellow oil with same NMR data as for protected precursor of 34. Compound 37 is obtained after treatment with 3M HCl (5 mL) for 16 h at room temperature, followed by solvent evaporation with same NMR data as for 34. $[\alpha]^{24}_D$−63.2 (c 0.3, $H_2O$).

Compound 38 (Scheme 6). Following the general procedure B, alkyne 3 (200 mg, 0.61 mmol) and azide 12a (160 mg, 0.61 mmol) in 1:1 $H_2O$/t-BuOH (2.5 mL) give, after work-up and chromatographic purification (4:1 EtOAc-petr. et., Rf=0.38), protected adduct (215 mg, 60%), precursor of 38, as a yellow oil with same NMR data as for protected precursor of 35. Compound 38 is obtained after treatment with 3M HCl (5 mL) for 16 h at room temperature, followed by solvent evaporation with same NMR data as for 35. $[\alpha]^{21}_D$ –63.5 (c 0.6, $H_2O$).

Compound 39. Following the general procedure B, alkyne 4 (222 mg, 0.61 mmol) and azide 13b (186 mg, 0.61 mmol) in 1:1 $H_2O$/t-BuOH (2 mL) give, after work-up and chromatographic purification (10:1 $CH_2Cl_2$/MeOH, Rf=0.47), protected adduct (201 mg, 49%), precursor of 39, as a yellow oil. $^1H$ NMR ($CDCl_3$, 200 MHz) δ 7.63 (s, 1H), 7.37 (br, 1H), 7.20 (m, 5H), 5.33 (m, 1H), 5.01 (s, 2H), 3.65 (s, 2H), 3.51 (m, 4H), 2.68 (m, 2H), 2.51 (m, 4H), 1.46 (s, 18H), 1.28 (s, 9H) ppm; $^{13}C$ NMR ($CDCl_3$, 50 MHz) δ 169.7 (s), 164.1 (s), 162.8 (s), 154.4 (s), 144.0 (s), 139.7 (s), 137.2 (s), 128.3 (d), 127.5 (d), 126.1 (d), 124.3 (d), 88.7 (s), 81.2 (s), 80.0 (s), 52.6 (t), 52.4 (t), 52.1 (t), 50.2 (d), 46.4 (t), 41.0 (t), 28.2 (q), 27.9 (q), 27.6 (q) ppm. Compound 39 is obtained after treatment with 3M HCl (5 mL) for 16 h at room temperature, followed by solvent evaporation. $[\alpha]^{24}_D$ +49.3 (c 0.6, $H_2O$). $^1H$ NMR ($D_2O$, 400 MHz) δ 7.96 (s, 1H), 7.33-7.27 (m, 5H), 5.23 (s, 2H), 5.17 (t, J=6.8 Hz, 2H), 3.87 (s, 2H), 3.45 (m, 4H), 3.21 (m, 2H), 2.67 (m, 4H) ppm.

Compound 40. Following the general procedure B, alkyne 5 (319 mg, 0.84 mmol) and azide 13a (221 mg, 0.84 mmol) in 1:1 $H_2O$/t-BuOH (3.5 mL) give, after work-up and chromatographic purification (12:1 $CH_2Cl_2$-MeOH, Rf=0.46), protected adduct (297 mg, 55%), precursor of 40, as a yellow oil. $^1H$ NMR ($CDCl_3$, 200 MHz) δ 7.54 (s, 1H), 7.30-7.20 (m, 5H), 5.38 (m, 1H), 5.03 (s, 2H), 3.58 (m, 4H), 3.58 (s, 3H), 2.94 (m, 2H), 2.81 (m, 2H), 2.71 (m, 2H), 2.56 (m, 4H), 1.48 (s, 18H) ppm; $^{13}C$ NMR ($CDCl_3$, 50 MHz) δ 170.8 (s), 164.4 (s), 162.8 (s), 154.6 (s), 146.4 (s), 139.5 (s), 137.2 (s), 128.6 (d), 127.7 (d), 126.0 (d), 122.8 (d), 88.7 (s), 81.2 (s), 57.3 (t), 52.9 (t), 52.5 (t), 52.0 (q), 50.0 (d), 46.8 (t), 39.7 (t), 28.2 (q), 23.3 (t) ppm. Compound 40 is obtained after treatment with 3M HCl (5 mL) for 16 h at room temperature, followed by solvent evaporation. $[\alpha]^{24}_D$ +57.4 (c 0.3, $H_2O$). $^1H$ NMR ($D_2O$, 400 MHz) δ 7.95 (s, 1H), 7.49-7.40 (m, 5H), 5.35-5.31 (m, 3H), 3.82 (m, 4H), 3.67-3.56 (m, 6H), 3.30 (t, J=7.2 Hz, 2H), 2.99 (d, J=7.2 Hz, 2H) ppm.

Compound 41. Following the general procedure B, alkyne 4 (117 mg, 0.32 mmol) and azide 12b (98 mg, 0.32 mmol) in 1:1 $H_2O$/t-BuOH (1.5 mL) give, after work-up and chromatographic purification (10:1 $CH_2Cl_2$-MeOH, Rf=0.47), protected adduct (93 mg, 43%), precursor of 41, as a yellow oil with same NMR data as for protected precursor of 39. Compound 41 is obtained after treatment with 3M HCl (5 mL) for 16 h at room temperature, followed by solvent evaporation with same NMR data as for 39. $[\alpha]^{24}_D$ –70.8 (c 0.6, $H_2O$).

Compound 42. Following the general procedure B, alkyne 5 (361 mg, 0.95 mmol) and azide 12a (250 mg, 0.95 mmol) in 1:1 $H_2O$/t-BuOH (4 mL) give, after work-up and chromatographic purification (12:1 $CH_2Cl_2$-MeOH, Rf=0.46), protected adduct (400 mg, 65%), precursor of 42, as a yellow oil with same NMR data as for protected precursor of 40. Compound 42 is obtained after treatment with 3M HCl (5 mL) for 16 h at room temperature, followed by solvent evaporation with same NMR data as for 40. $[\alpha]^{24}_D$ –55.2 (c 0.3, $H_2O$).

Compound 43. Following the general procedure B, alkyne 1 (165 mg, 0.55 mmol) and azide 11 (160 mg, 0.55 mmol) in 1:1 $H_2O$/t-BuOH (2 mL) give, after work-up and chromatographic purification (2:1 EtOAc-petr. et., Rf=0.56), protected adduct (177 mg, 55%), precursor of 43, as a yellow oil. $^1H$ NMR ($CDCl_3$, 200 MHz) δ 11.41 (br, 1H), 8.71 (br, 1H), 7.68 (s, 1H), 7.40 (m, 5H), 4.92 (s, 2H), 4.66 (d, J=6.0 Hz, 2H), 4.23 (s, 2H), 1.45 (s, 9H), 1.42 (s, 9H), 1.41 (s, 9H) ppm; $^{13}C$ NMR ($CDCl_3$, 50 MHz) δ 167.1 (s), 164.9 (s), 163.0 (s), 155.6 (s), 152.5 (s), 143.4 (s), 140.5 (s), 130.0 (d), 129.0 (d), 127.7 (d), 123.7 (d), 82.9 (s), 82.1 (s), 79.0 (s), 52.2 (t), 50.9 (t), 36.2 (t), 28.1 (q), 27.8 (q), 27.7 (q) ppm. MS m/z 353 (4.5), 266 (1.6), 151 (23), 106 (100), 77 (57), 57 (7). Compound 43 is obtained after treatment with 3M HCl (5 mL) for 16 h at room temperature, followed by solvent evaporation. $^1H$ NMR ($D_2O$, 400 MHz) δ 7.88 (s, 1H), 7.55-7.47 (m, 5H), 5.23 (s, 2H), 4.51 (s, 2H), 4.49 (s, 2H) ppm.

Compound 44. Following the general procedure B, alkyne 2 (200 mg, 0.64 mmol) and azide 11 (186 mg, 0.64 mmol) in 1:1 $H_2O$/t-BuOH (2.6 mL) give, after work-up and chromatographic purification (4:1 EtOAc-petr. et., Rf=0.69), protected adduct (228 mg, 59%), precursor of 44, as a white solid. $^1H$ NMR ($CDCl_3$, 200 MHz) δ 7.62 (s, 1H), 7.44 (m, 5H), 4.91 (s, 2H), 4.27 (s, 2H), 4.18 (m, 2H), 3.02 (m, 2H), 1.48 (s, 9H), 1.46 (s, 9H), 1.44 (s, 9H) ppm; $^{13}C$-NMR ($CDCl_3$, 50 MHz) δ 167.1 (s), 165.1 (s), 163.1 (s), 160.0 (s), 154.6 (s), 143.2 (s), 140.7 (s), 130.1 (d), 129.0 (d), 127.8 (d), 123.3 (d), 83.9 (s), 82.2 (s), 78.7 (s), 52.4 (t), 50.9 (t), 44.3 (t), 28.4 (q), 28.1 (q), 28.0 (q), 25.4 (t) ppm. MS m/z 601 ($M^+$, 0.3), 501 (0.9), 401 (3.7), 106 (11), 77 (4), 57 (49), 41 (100). Compound 44 is obtained after treatment with 3M HCl (5 mL) for 16 h at room temperature, followed by solvent evaporation. $^1H$ NMR ($D_2O$, 400 MHz) δ 7.82 (s, 1H), 7.58-7.50 (m, 5H), 5.24 (s, 2H), 4.51 (s, 2H), 3.51 (m, 2H), 3.00 (m, 2H) ppm.

Compound 45. Following the general procedure B, alkyne 3 (197 mg, 0.61 mmol) and azide 11 (176 mg, 0.61 mmol) in 1:1 $H_2O$/t-BuOH (2.4 mL) give, after work-up and chromatographic purification (4:1 EtOAc-petr. et., Rf=0.75), protected adduct (232 mg, 62%), precursor of 45, as a yellow oil. $^1H$ NMR ($CDCl_3$, 200 MHz) δ 9.30 (br, 2H), 7.63 (s, 1H), 7.48 (m, 5H), 4.92 (s, 2H), 4.27 (s, 2H), 3.95 (m, 2H), 2.74 (m, 2H), 1.95 (m, 2H), 1.48 (s, 9H), 1.47 (s, 9H), 1.43 (s, 9H) ppm; $^{13}C$ NMR ($CDCl_3$, 50 MHz) δ 167.0 (s), 165.1 (s), 163.4 (s), 160.4 (s), 154.7 (s), 146.3 (s), 140.6 (s), 130.7 (d), 129.0 (d), 127.8 (d), 122.7 (d), 83.7 (s), 82.1 (s), 78.5 (s), 52.3 (t), 51.0 (t), 44.1 (t), 28.3 (q), 28.1 (q), 28.0 (q), 23.0 (t), 21.8 (t) ppm. MS m/z 615 ($M^+$, 0.2), 515 (0.5), 343 (20), 287 (15), 106 (22), 77 (9), 57 (100). Compound 45 is obtained after treatment with 3M HCl (5 mL) for 16 h at room temperature, followed by solvent evaporation. $^1H$ NMR ($D_2O$, 400 MHz) δ 7.78 (s, 1H), 7.60-7.50 (m, 5H), 5.25 (s, 2H), 4.52 (s, 2H), 3.23 (t, J=6.8 Hz, 2H), 2.80 (t, J=7.2 Hz, 2H), 1.97 (m, 2H) ppm.

Compound 46. Following the general procedure B, alkyne 5 (372 mg, 0.98 mmol) and azide 11 (284 mg, 0.98 mmol) in 1:1 $H_2O$/t-BuOH (4 mL) give, after work-up and chromatographic purification (12:1 $CH_2Cl_2$-MeOH, Rf=0.46), protected adduct (450 mg, 68%), precursor of 46, as an orange solid. $^1H$ NMR ($CDCl_3$, 200 MHz) δ 7.59 (s, 1H), 7.45 (m, 5H), 4.94 (s, 2H), 4.28 (s, 2H), 3.62 (m, 4H), 2.90 (m, 2H), 2.70 (m, 2H), 2.57 (m, 4H), 1.48 (s, 9H), 1.47 (s, 9H), 1.44 (s, 9H) ppm. Compound 46 is obtained after treatment with 3M HCl (5 mL) for 16 h at room temperature, followed by solvent evaporation. $^1H$ NMR ($D_2O$, 400 MHz) δ 8.01 (s, 1H), 7.53-7.34 (m, 5H), 5.2 (s, 2H), 4.44 (s, 2H), 4.07 (m, 2H), 3.75 (m, 2H), 3.65 (m, 2H), 3.57 (m, 4H), 3.25 (m, 4H) ppm.

Compound 47. Following the general procedure B, alkyne 2 (140 mg, 0.45 mmol) and azide 15 (125 mg, 0.45 mmol) in 1:1 $H_2O$/t-BuOH (2.0 mL) give, after work-up and chromatographic purification (4:1 EtOAc-petr. et., Rf=0.43), protected adduct (159 mg, 60%), precursor of 47, as a yellow oil. $^1H$ NMR ($CDCl_3$, 200 MHz) δ 9.24 (br, 1H), 7.69 (s, 1H), 7.29-7.14 (m, 2H), 7.01-6.93 (m, 5H), 5.35 (m, 1H), 5.01 (s, 2H), 4.18 (m, 2H), 3.57 (s, 3H), 3.05 (m, 2H), 2.80 (m, 2H), 1.49 (s, 9H), 1.47 (s, 9H) ppm; $^{13}C$ NMR ($CDCl_3$, 50 MHz) δ

170.5 (s), 164.3 (s), 161.6 (d, $J_{CF}$=163 Hz), 159.4 (s), 154.4 (s), 145.4 (s), 135.5 (s), 127.8 (dd, $J_{CF}$=8.3 Hz, 2C), 123.4 (s), 115.4 (dd, $J_{CF}$=22 Hz, 2C), 84.0 (s), 78.8 (s), 52.8 (t), 51.9 (q), 49.5 (d), 44.1 (t), 39.8 (t), 28.3 (q), 28.0 (q), 25.3 (t) ppm. Compound 47 is obtained after treatment with 3M HCl (5 mL) for 16 h at room temperature, followed by solvent evaporation. $[\alpha]^{24}_D$+55.2 (c 0.5, H$_2$O). $^1$H NMR (D$_2$O, 400 MHz) δ 7.86 (s, 1H), 7.41 (dd, J=8.8, 5.2 Hz, 2H), 7.16 (t, J=8.8 Hz, 2H), 5.31 (m, 1H), 5.26 (d, J=4.4 Hz, 2H), 3.52 (t, J=6.8 Hz, 2H), 3.04-2.97 (m, 4H) ppm.

Compound 48. Following the general procedure B, alkyne 3 (146 mg, 0.45 mmol) and azide 15 (125 mg, 0.45 mmol) in 1:1 H$_2$O/t-BuOH (2.0 mL) give, after work-up and chromatographic purification (4:1 EtOAc-petr. et., Rf=0.6), protected adduct (96 mg, 37%), precursor of 48, as a yellow oil. $^1$H NMR (CDCl$_3$, 200 MHz) δ 9.34 (br, 1H), 7.86 (br, 1H), 7.19-7.12 (m, 3H), 6.99-6.90 (m, 2H), 5.33 (m, 1H), 5.03 (s, 2H), 3.88 (m, 2H), 3.55 (s, 3H), 2.77 (t, 4H), 2.03 (m, 2H), 1.48 (s, 9H), 1.46 (s, 9H) ppm. Compound 48 is obtained after treatment with 3M HCl (2 mL) for 16 h at room temperature, followed by solvent evaporation. $[\alpha]^{24}_D$+59.2 (c 0.3, H$_2$O). $^1$H NMR (D$_2$O, 400 MHz) δ 7.81 (s, 1H), 7.42 (dd, J=8.8, 5.2 Hz, 2H), 7.17 (t, J=8.8 Hz, 2H), 5.32 (m, 1H), 5.26 (d, J=2.8 Hz, 2H), 3.22 (t, J=6.4 Hz, 2H), 3.00 (m, 2H), 2.82 (t, J=7.4 Hz, 2H), 1.98 (m, 2H) ppm.

Compound 49. Following the general procedure B, alkyne 3 (117 mg, 0.36 mmol) and azide 14 (100 mg, 0.36 mmol) in 1:1 H$_2$O/t-BuOH (2.0 mL) give, after work-up and chromatographic purification (4:1 EtOAc-petr. et., Rf=0.6), protected 49 (88 mg, 34%) as a yellow oil with same NMR data as for precursor of 48. Compound 49 is obtained after treatment with 3M HCl (5 mL) for 16 h at room temperature, followed by solvent evaporation with same NMR data as for 48. $[\alpha]^{24}_D$−56.0 (c 0.3, H$_2$O).

Compound 50 (Scheme 7). Following the general procedure B, alkyne 7 (158 mg, 0.57 mmol) and azide 17 (107 mg, 0.57) in 1:1 H$_2$O/t-BuOH (1 mL) give, after work-up and chromatographic purification (2:1 EtOAc-Et$_2$O, Rf=0.3), adduct 61. $^1$H NMR (CDCl$_3$, 200 MHz) δ 8.18 (d, 1H), 7.53 (s, 1H), 7.30 (t, 2H), 7.05 (t, 2H), 5.43 (q, 1H), 5.03 (br, 1H), 4.41 (t, 2H), 3.71 (s, 2H), 3.64 (s, 3H), 3.61 (d, 2H), 3.09 (s, 2H), 2.92 (t, 2H), 2.33 (s, 3H), 1.40 (s, 9H) ppm. Successively, 61 is treated with a 1:1 TFA:CH$_2$Cl$_2$ mixture (3.8 mL) for 2 h at room temperature, followed by solvent evaporation, thus giving compound 62 in 93% yield. $^1$H NMR (D$_2$O, 200 MHz) δ 8.03 (br, 1H), 7.26 (s, 1H), 7.14 (t, 2H), 6.87 (t, 2H), 5.02 (m, 1H), 4.53 (d, 2H), 4.29 (s, 3H), 3.80 (s, 2H), 3.38 (s, 2H), 3.31 (d, 2H), 2.68 (dd, 2H), 2.65 (s, 3H), 2.00 (s, 3H) ppm. To a solution of 62 (150 mg, 0.40 mmol) and triethylamine (62 μL, 0.40 mmol) in anhydrous CH$_2$Cl$_2$ (2 mL) a solution of N,N'-di-Boc-N''-triflylguanidine (171 mg, 0.40 mmol) in anhydrous CH$_2$Cl$_2$ (2 mL) is added, and the mixture is left reacting for 16 h at room temperature. After solvent evaporation and chromatographic purification (1:1 EtOAc-Et$_2$O, Rf=0.14), compound 63 (55 mg, 0.09 mmol) is obtained in 25% yield. $^1$H NMR (CDCl$_3$, 200 MHz) δ 11.40 (s, 1H), 9.20 (d, 1H), 8.48 (m, 1H), 8.39 (d, 1H), 7.68 (t, 1H), 7.31 (t, 2H), 7.06 (t, 2H), 5.40 (q, 1H), 4.61 (t, 2H), 3.92 (q, 2H), 3.74 (s, 2H), 3.62 (s, 3H), 3.18 (s, 2H), 2.37 (s, 3H), 1.51 (s, 9H), 1.47 (s, 9H) ppm. Compound 50 is achieved in quantitative yield after treatment of 63 (55 mg, 0.09 mmol) with 3M HCl (1 mL) for 16 h at room temperature, followed by solvent evaporation. $^1$H NMR (D$_2$O, 200 MHz) δ 8.09 (s, 1H), 7.21 (m, 2H), 6.95 (t, J=8.7 Hz, 2H), 5.10 (t, J=5.7 Hz, 1H), 4.48-4.40 (m, 6H), 3.91 (s, 2H), 3.55 (m, 2H), 2.78 (s, 3H) ppm; $^{13}$C NMR (D$_2$O, 50 MHz) d 173.5 (s), 163.6 (s), 163.2 (s), 157.3 (d, $J_{CF}$=140 Hz), 135.2 (s), 134.5 (s), 127.4 (d, 2C), 127.3 (s), 114.8 (dd, $J_{CF}$=11 Hz, 2C), 55.0 (d), 49.5 (q), 49.3 (t), 48.6 (t), 44.7 (t), 40.6 (t), 39.9 (t), 39.1 (t). $[\alpha]^{24}_D$+18.6 (c 0.3, H$_2$O).

Compound 51. Compound 51 is prepared according to the procedure for the synthesis of 50, starting from alkyne 6 (122 mg, 0.65 mmol) and azide 17 (180 mg, 0.65 mmol), with same NMR data as for 50. $[\alpha]^{24}_D$+23.2 (c 0.3, H$_2$O).

Compound 52. Following the general procedure C, alkyne 2 (100 mg, 0.306 mmol), azide 20 (80 mg, 0.306 mmol) and iodo(triethylphosphite)Cu (11 mg, 0.0306 mmol) in anhydrous THF (2 mL) give, after purification (2:1 EtOAc-petr. et. Rf=0.35), protected adduct as a yellow oil (140 mg, 86% yield). $^1$H NMR (CDCl$_3$, 200 MHz) δ 9.45 (br, 1H), 9.35 (br, 1H), 7.68 (d, 2H), 7.55 (s, 1H), 7.31 (d, 2H), 4.62 (pt, 2H), 4.38 (pt, 2H), 4.13 (q, 2H), 3.83 (s, 2H), 3.68 (t, 2H), 3.02 (pt, 2H), 2.43 (s, 3H), 1.52 (s, 9H), 1.46 (s, 9H), 1.25 (t, 3H) ppm. Compound 52 is obtained after treatment with 3M HCl (3 mL) for 16 h at 30° C., followed by solvent evaporation. $^1$H NMR (D$_2$O, 200 MHz) δ 7.70 (s, 1H), 7.44 (d, 2H), 7.24 (d, 2H), 4.44 (t, 2H), 3.98 (t, 2H), 3.67 (pt, 2H), 3.33 (t, 2H), 2.79 (t, 2H), 2.28 (s, 3H) ppm.

Compound 53. Following the general procedure C, alkyne 3 (100 mg, 0.306 mmol), azide 20 (830 mg, 0.306 mmol) and iodo(triethylphosphite)Cu (11 mg, 0.0306 mmol) in anhydrous THF (3 mL) give, after purification (2:1 EtOAc-petr. et., Rf=0.35), protected adduct as a yellow oil (140 mg, 84% yield). $^1$H NMR (CDCl$_3$, 200 MHz) δ 9.40 (br, 21H), 7.67 (d, 2H), 7.58 (s, 1H), 7.29 (d, 2H), 4.60 (t, 2H), 4.05 (q, 2H), 3.93 (t, 2H), 3.83 (s, 2H), 3.72 (t, 2H), 2.75 (t, 2H), 2.42 (s, 3H), 1.97 (s, 3H), 1.51 (s, 9H), 1.49 (s, 9H), 1.15 (t, 3H) ppm. Compound 53 is obtained after treatment with 3M HCl (5 mL) for 16 h at 30° C., followed by solvent evaporation. $^1$H NMR (D$_2$O, 200 MHz) δ 7.67 (s, 1H) 7.42 (d, 2H), 7.22 (d, 2H), 4.43 (t, 2H), 4.00 (t, 2H), 3.67 (pt, 2H), 3.04 (t, 2H), 2.57 (t, 2H), 2.28 (s, 3H), 1.76 (t, 2H) ppm. $^{13}$C NMR (D$_2$O, 50 MHz) δ 168.4 (s), 163.7 (s), 160.6 (s), 154.9 (s), 143.9 (s), 135.6 (d), 129.7 (d), 127.3 (d), 61.4 (t), 49.8 (t), 49.6 (t), 48.9 (t), 44.1 (t), 28.3 (t), 28.0 (q) ppm.

Compound 54. Following the general procedure C, alkyne 3 (189 mg, 0.68 mmol), azide 16 (200 mg, 0.615 mmol) and iodo(triethylphosphite)Cu (24 mg, 0.068 mmol) in anhydrous THF (4 mL) give, after purification (5:1 EtOAc-petr. et., Rf=0.48), protected adduct as a yellow oil (88% yield). $^1$H NMR (CDCl$_3$, 200 MHz) δ 9.45 (br, 1H), 8.02 (br, 1H), 7.35 (br, 1H), 7.62 (s, 1H), 7.00 (d, 2H), 6.72 (d, 2H), 5.38-5.22 (m, 1H), 5.00 (s, 2H), 3.85 (m, 2H), 3.50 (s, 3H), 2.90-2.60 (m, 4H), 1.95 (m, 2H), 1.45 (s, 9H), 1.39 (s, 9H) ppm. Compound 54 is obtained after treatment with 3M HCl (3 mL) for 16 h at room temperature, followed by solvent evaporation. $^1$H NMR (D$_2$O, 200 MHz) δ 7.63 (s, 1H), 7.10 (d, 2H), 6.72 (d, 2H), 5.10-5.05 (m, 1H), 5.06 (s, 2H), 3.02 (t, 2H), 3.78 (d, 2H), 2.62 (t, 2H), 1.78 (m, 2H) ppm.

Compound 55. Following the general procedure B, alkine 3 (200 mg, 0.62 mmol) and azide 18 (170 mg, 0.62 mmol) in 1:1 H$_2$O/t-BuOH (5 mL) give, after purification (30:1 CH$_2$Cl$_2$-methanol, Rf=0.7), protected adduct as a yellow oil. $^1$H-NMR (CDCl$_3$, 200 MHz) δ 9.34 (sb, 2H), 7.77 (s, 1H), 6.72 (sb, 1H), 4.95 (s, 2H), 3.91 (q, 2H), 3.62 (s, 3H), 3.49 (q, 2H), 2.76 (t, 2H), 2.50 (t, 2H), 2.14-1.90 (m, 2H), 1.47 (s, 9H), 1.46 (s, 9H). Compound 55 is obtained after treatment with 3M HCl (5 mL) for 16 h at room temperature, followed by solvent evaporation. $^1$H NMR (D$_2$O, 200 MHz) δ 7.84 (s, 1H), 5.10 (s, 2H), 3.36 (t, 2H), 3.08 (t, 2H), 2.75-2.62 (m, 2H), 2.47 (t, 2H), 1.83 (t, 2H) ppm. $^{13}$C NMR (D$_2$O, 50 MHz) δ 177.8 (s), 166.9 (s), 156.7 (s), 146.0 (s), 126.1 (d), 52.9 (t), 42.2 (t), 38.9 (t), 31.0 (t), 27.0 (t), 21.0 (t) ppm.

Compound 56. Following the general procedure B, alkine 3 (200 mg, 0.62 mmol) and azide 19 (132 mg, 0.62 mmol) in 1:1 H$_2$O/t-BuOH (5 mL) give, after purification (1:1 EtOAc-petr. et., Rf=0.7), protected adduct as a yellow oil. $^1$H NMR (CDCl$_3$, 200 MHz) δ 9.50 (sb, 1H), 7.95 (s, 1H), 5.15 (s, 2H), 4.25 (q, 2H), 4.11-4.08 (m, 2H), 3.45-3.41 (m, 2H), 2.94 (t, 2H), 2.44 (t, 2H), 2.41 (s, 1H), 2.17-2.15 (m, 2H), 1.96-1.91 (m, 2H), 1.65 (s, 9H), 1.64 (s, 9H), 1.37 (t, 3H) ppm. Compound 56 is obtained after treatment with 3M HCl (5 mL) for 16 h at room temperature, followed by solvent evaporation. $^1$H NMR (D$_2$O, 200 MHz) δ 7.92 (s, 1H), 5.14 (s, 2H), 3.15-3.04 (m, 4H), 2.71 (t, 2H), 2.20 (t, 2H), 1.85-1.78 (m, 2H), 1.68-1.61 (m, 2H) ppm. $^{13}$C NMR (D$_2$O, 50 MHz) δ 177.8 (s), 166.9 (s), 156.7 (s), 146.0 (s), 126.1 (d), 52.9 (t), 42.2 (t), 38.8 (t), 31.0 (t), 27.0 (t), 23.7 (t), 21.0 (t) ppm.

Compound 57. Following the general procedure B, alkyne 10 (73 mg, 0.26 mmol) and azide 14 (108 mg, 0.26 mmol) in H$_2$O/t-BuOH 1:1 (35 mL) give, after purification (3:1 EtOAc-petr. et., Rf=0.55), protected adduct as a yellow oil (75 mg, 42% yield). $^1$H NMR (CDCl$_3$, 200 MHz) δ 7.85 (s, 1H), 7.72-7.45 (m, 4H), 7.22 (s, 1H), 7.22-7.15 (m, 2H), 7.00-6.96 (m, 2H), 5.25 (q, 1H), 5.05 (s, 2H), 3.95-3.85 (m, 2H), 3.56 (s, 3H), 3.83 (t, 4H), 2.04 (s, 2H), 1.50 (s, 9H), 1.48 (s, 9H), 1.25 (t, 2H) ppm. Compound 57 is obtained after treatment with 3M HCl (3 mL) for 16 h at room temperature, followed by solvent evaporation. $^1$H NMR (D$_2$O, 200 MHz) δ 7.75-7.65 (m, 1H), 7.65 (s, 1H), 7.58-7.35 (m, 3H), 7.28-7.17 (m, H), 7.05-6.91 (m, 2H), 5.16-5.08 (m, 1H), 5.07 (s, 2H), 3.05 (t, 3H), 2.81 (d, 2H), 2.66 (t, 3H), 1.84-1.70 (m, 2H). $^{13}$C NMR (D$_2$O, 50 MHz) δ 173.6 (s), 165.9 (s), 161.1 (d, $J_{C-F}$=243.50), 155.8 (s), 145.9 (s), 134.9 (d, $J_{C-F}$=2.75), 132.30 (s), 131.1 (s), 130.9 (d), 128.2 (d), 127.9 (d), 127.3 (d, $J_{C-F}$=31.20), 126.3 (d), 124.0 (d), 114.9 (d), 114.5 (d), 113.4 (d), 51.4 (d), 49.3 (t), 39.4 (t), 38.9 (t), 26.5 (t), 20.6 (t) ppm.

Compound 58. Following the general procedure C, alkyne 9 (400 mg, 0.718 mmol), azide 12a (209 mg, 0.79 mmol) and iodo(triethylphosphite)Cu (28 mg, 0,079 mmol) in anhydrous THF (4 mL) give, after purification (5:1 CH$_2$Cl$_2$—CH$_3$OH, Rf=0.35), protected adduct as a yellow oil (120 mg, 20% yield). $^1$H NMR (CDCl$_3$, 200 MHz) δ 7.52 (s, 1H), 7.38-7.18 (m, 5H), 5.43-5.37 (m, 1H), 5.03 (s, 2H), 3.75-3.20 (m, 6H), 3.58 (s, 3H), 3.20-3.05 (m, 4H), 2.90-2.63 (m, 2H), 2.45-2.35 (m, 1H), 2.20-1.80 (m, 4H), 1.85-1.05 (m, 8H), 1.47 (s, 9H), 1.43 (s, 9H) ppm. Compound 58 is obtained after treatment with 3M HCl (5 mL) for 16 h at 30° C., followed by solvent evaporation. $^1$H NMR (D$_2$O, 200 MHz) δ 7.67 (s, 1H), 7.34-7.18 (m, 5H), 5.18-5.12 (m, 1H), 5.09 (s, 2H), 3.75-3.70 (m, 2H), 3.30-2.95 (m, 4H), 2.90-2.75 (m, 4H), 2.75-2.60 (m, 3H), 2.30-2.00 (m, 4H), 1.95-1.80 (m, 2H), 1.50-1.25 (m, 2H), 1.20-1.05 (m, 4H) ppm.

Compound 59. Following the general procedure C, alkyne 8 (280 mg, 0.69 mmol), azide 12a (182 mg, 0.69 mmol) and iodo(triethylphosphite)Cu (25 mg, 0.069 mmol) in anhydrous THF (4 mL) give, after purification (EtOAc, Rf=0.53), protected adduct as a yellow oil (364 mg, 82% yield). $^1$H NMR (CDCl$_3$, 200 MHz) δ 9.50 (d, 1H), 7.37 [s, 1H), 7.31-7.18 (m, 5H), 6.93 (d, 2H), 6.48 (d, 2H), 5.45-5.38 (m, 1H), 5.02 (s, 2H), 3.62 (s, 3H), 3.52 (t, 2H), 3.40 (m, 2H), 3.00-2.90 (m, 2H), 2.75 (t, 2H), 2.45 (t, 2H), 1.70-1.50 (m, 2H), 1.45 (s, 9H), 1.39 (s, 9H) ppm. Compound 59 is obtained after treatment with 3M HCl (5 mL) for 16 h at 30° C., followed by solvent evaporation. $^1$H NMR (D$_2$O, 200 MHz) δ 7.54 (s, 1H), 7.26-7.18 (m, 5H), 6.93 (d, 2H), 6.60 (d, 2H), 5.18-5.0 5 (m, 1H), 5.06 (s, 2H), 3.32 (t, 2H), 2.90 (m, 2H), 2.80 (d, 2H), 2.58 (t, 2H), 2.48 (t, 2H), 1.70-1.60 (m, 2H) ppm.

Solid-phase receptor binding assay. [$^{125}$I]-Echistatin, labelled according to the lactoperoxidase method and with a specific activity of 2000 Ci/mmol, and αvβ3 and αvβ5 integrins, purified from human placenta, are used for the in vitro assays. Purified αvβ3 and αvβ5 receptors are respectively diluted to 500 ng/mL and 1000 ng/mL in 20 mM Tris (pH 7.4), 150 mM NaCl, 2 mM CaCl$_2$, 1 mM MgCl$_2$, 1 mM MnCl$_2$. An amount of the diluted receptor solutions (100 μL/well) is added to a 96-well microtiter plate (Optiplate-96 HB, PerkinElmer Life Sciences, Boston, Mass.) and incubated at 4° C. for 16 h. Then, the plate is washed once with an incubation buffer [20 mM Tris (pH 7.4), 150 mM NaCl, 2 mM CaCl$_2$, 1 mM MgCl$_2$, 1 mM MnCl$_2$, 1% BSA] and incubated for additional 2 h at room temperature. The plate is treated twice with the same buffer, and competitive binding experiments are carried out with a fixed concentration of [$^{125}$I]-Echistatin (0.05 nM and 0.1 nM for αvβ3 and αvβ5 respectively) and concentrations of the test compounds ranging from 0.01 nM to 100 μM. All the assays are carried out in triplicate at a final volume of 0.2 mL, each containing the following species: 0.05 mL of [$^{125}$I]-Echistatina, 0.04 mL of the test compounds, and 0.11 mL of the incubation buffer. Non-specific binding is defined as the [$^{125}$I]-Echistatin bound in the presence of excess (1 μM) of non-labelled echistatin. After an incubation period of 3 h at room temperature, the plate is washed three times with the incubation buffer, then the radioactivity is measured in a plate counter Top-Count NXT (Perkin Elmer Life Sciences, Boston, Mass.) using 200 μL/well of scintillating liquid MicroScint-40 (PerkinElmer Life Sciences, Boston, Mass.). Data analysis. IC$_{50}$ values are determined by fitting the binding inhibition data with a non-linear regression, using the GraphPad Prism 4.0 software package (GraphPad Prism, San Diego, Calif.). Moreover, where the curves show a Hill slope significantly lower than the unit (K<-0.80), the data are further analyzed according to a two-sites model. The inhibition curves better fitted according to a two-sites model (p<0.05) rather than a single-site model are considered to be significant.

Melanoma cell line assay. The selected cell line for this study is the A375M, which are in vivo selected melanoma cells starting from A375P cells isolated from a amelanotic human melanoma. The expression of the RGD-dependent integrinic pattern, comprising αvβ3, αvβ5, α5β1 integrins, of A375M cells is determined by the flux cytometry technique (FACScanto, Becton & Dickinson) and by RT-PCR. With aim to evaluate the ability of compounds of formula (I) of binding to integrins exposed to the melanoma cells surface, the inhibition of adhesion of such cells to vitronectin, fibronectin and osteopontin are measured. A spectrophotometric evaluation of the cellular content of the culture plates used in the adhesion tests allows for the precision and the correlation of the results obtained in different experiments.

The invention claimed is:
1. A compound of formula (Ia)

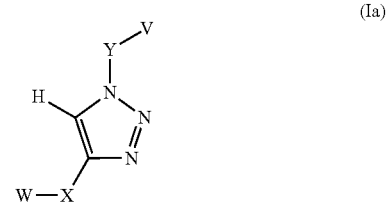

wherein

V is a COOH group;

W is a guanidino group or an isostere chosen from the group consisting of

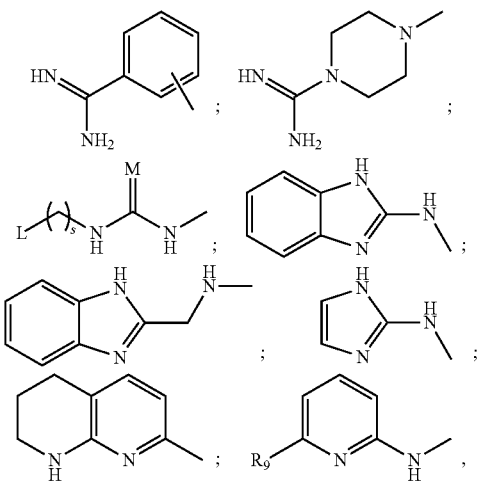

where M=NH; L=H, cycloalkyl, aryl optionally substituted, NH$_2$, OH, SH, tyrosine, tyramine,

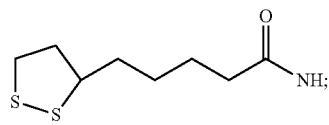

and s=0-8; R$_9$=H, NH$_2$, CH$_3$, CF$_3$;

V—Y— is chosen in the group consisting of V—(CH$_2$)p-CH(R$_5$)—N(R$_4$)—(CH$_2$)$_m$—, V—(CH$_2$)p-CH(R$_5$)—N(R$_4$)—CO—(CH$_2$)$_m$—, wherein m=1,2,3; p=0,1,2; R$_4$=H, an alkyl of C$_1$-C$_4$, phenyl optionally substituted with one selected from the group consisting of an alkyl of C$_1$-C$_4$, a halo group, a hydroxyl group, and a combination thereof, SO$_2$-phenyl optionally substituted with one selected from the group consisting of an alkyl of C$_1$-C$_4$, a halo group, a hydroxyl group, and a combination thereof; R$_5$=H, amino acid side chain, or is a ring structure chosen from the group consisting of

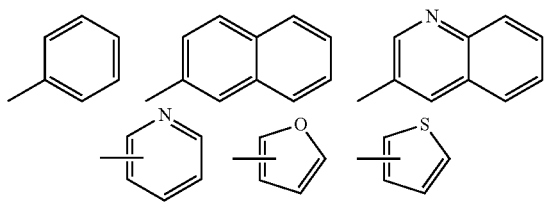

said ring structure being optionally substituted with one selected from the group consisting of an alkyl of C$_1$-C$_4$, a halo group, a hydroxyl group, and a combination thereof; and W—X— is chosen from the group consisting of W—(CH$_2$)n-, where n=1,2,3;

including all the possible variations of the stereogenic centers, pharmaceutically acceptable salts, and including the possible presence of one or more radioisotopes.

2. Compounds of formula (Ia) according to claim 1

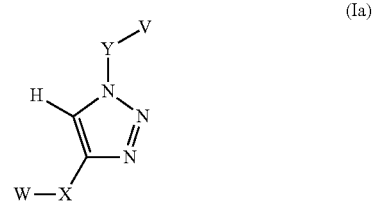

(Ia)

wherein

W—X— is chosen in the group consisting of W—(CH$_2$)n-, where n=1,2,3;

V—Y— is chosen in the group consisting of V—(CH$_2$)p-CH(R$_5$)—N(R$_4$)—CO—CH$_2$—, V—(CH$_2$)p-CH(R$_5$)—N(R$_4$)—(CH$_2$)$_m$—, where m e p are independently=0,1,2; R$_4$=H, Me, Ph, SO$_2$-Ph optionally substituted with one selected from the group consisting of an alkyl of C$_1$-C$_4$, a halo group, a hydroxyl group, and a combination thereof; R$_5$=H, para-F-Ph, para-OH-Ph;

W is chosen in the group consisting of a guanidino group,

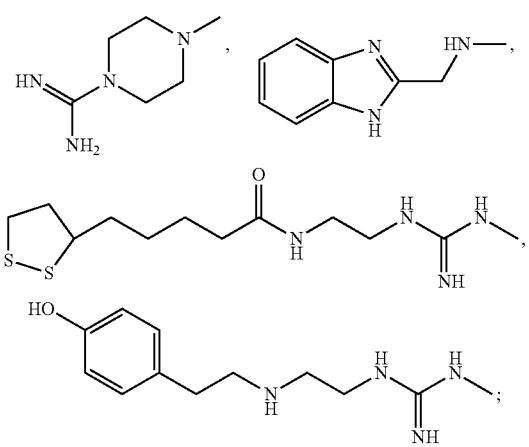

V is a COOH group.

3. Compounds of formula (Ia) according to claim 1

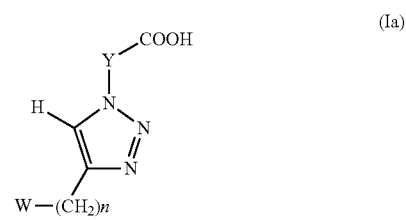

(Ia)

wherein n=1,2,3;

Y—COOH is chosen from the group consisting of;

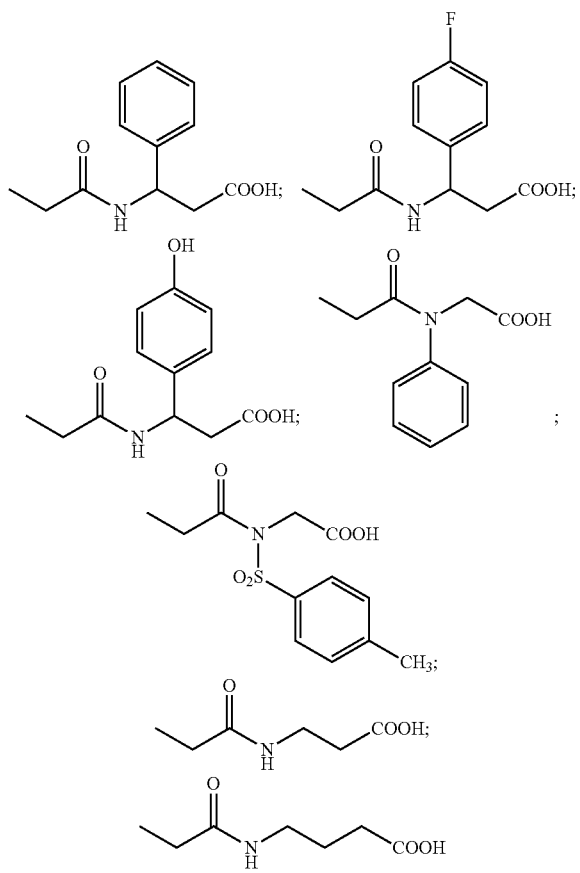

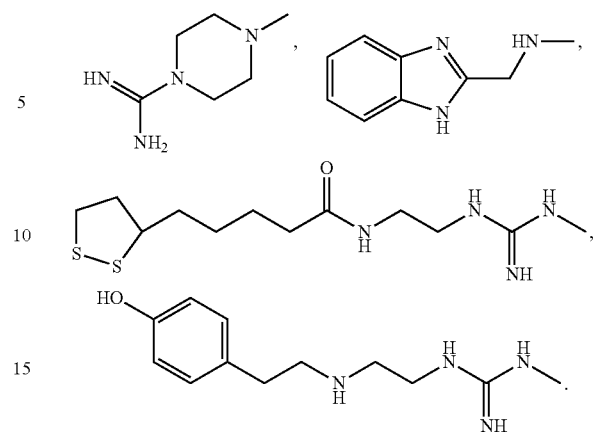

W is chosen from the group consisting of a guanidino group,

4. A process for the preparation of compounds of formula (Ia) according to claim 1, said process comprising a Huisgen 1,3-dipolar cycloaddition between an azide J-N$_3$ and an alkyne K—C≡CH, where J and K are respectively precursors of Y—V and X—W groups.

5. A method comprising administering a medicament and/or diagnostic compound of formula (Ia) according to claim 1 to a subject in need thereof.

6. A pharmaceutical composition comprising at least one compound of formula (Ia) according to claim 1 and at least another pharmaceutically acceptable ingredient.

7. A method for the preparation of compounds of formula (Ia) according to claim 1 labelled with radioisotopes, wherein said method comprises using compounds of formula (Ia) according to claim 1 as intermediates.

* * * * *